United States Patent
Tsao et al.

(10) Patent No.: US 12,221,494 B2
(45) Date of Patent: Feb. 11, 2025

(54) SHORT SYNTHETIC PEPTIDES AND THEIR USES FOR TREATING RETINAL DEGENERATIVE DISEASES AND/OR TISSUE INJURIES

(71) Applicant: MacKay Memorial Hospital, Taipei (TW)

(72) Inventors: Yeou-Ping Tsao, Taipei (TW); Tsung-Chuan Ho, Taipei (TW)

(73) Assignee: MacKay Memorial Hospital, Taipei (TW)

( * ) Notice: Subject to any disclaimer, the term of this patent is extended or adjusted under 35 U.S.C. 154(b) by 539 days.

(21) Appl. No.: 17/604,925

(22) PCT Filed: Aug. 27, 2019

(86) PCT No.: PCT/CN2019/102739
§ 371 (c)(1),
(2) Date: Oct. 19, 2021

(87) PCT Pub. No.: WO2021/035515
PCT Pub. Date: Mar. 4, 2021

(65) Prior Publication Data
US 2022/0204559 A1    Jun. 30, 2022

(51) Int. Cl.
| | | |
|---|---|---|
| *C07K 7/06* | (2006.01) | |
| *A61K 38/08* | (2019.01) | |
| *A61P 9/00* | (2006.01) | |
| *A61P 9/08* | (2006.01) | |
| *A61K 38/00* | (2006.01) | |

(52) U.S. Cl.
CPC ............... *C07K 7/06* (2013.01); *A61K 38/08* (2013.01); *A61P 9/00* (2018.01); *A61P 9/08* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 11,760,784 B2 * | 9/2023 | Lee | A61K 9/0048 514/20.8 |
| 2003/0032141 A1 * | 2/2003 | Nguyen | C12N 15/74 435/320.1 |
| 2021/0128685 A1 * | 5/2021 | Fan | A61P 27/02 |
| 2021/0221862 A1 * | 7/2021 | Lee | C07K 14/475 |

OTHER PUBLICATIONS

UniProt Accession No. A0A0A9A609, 4 pages (2015) (Year: 2015).*
UniProt Accession No. Q91529, 6 pages (2001) (Year: 2001).*
Kober et al., Biotechnol. Bioeng. 110:1164-1173 (2013) (Year: 2013).*
Auclair et al., Prot. Sci. 21:13-25 (2012) (Year: 2012).*
Shi et al., Biomacromol. 15:3559-3568 (2014) (Year: 2014).*

* cited by examiner

*Primary Examiner* — Thea D' Ambrosio
(74) *Attorney, Agent, or Firm* — NZ Carr Law Office

(57) ABSTRACT

Disclosed herein are synthetic peptides and compositions comprising the same, for the treatment of a retinal degenerative disease or tissue injury. Also disclosed herein are methods of treating a retinal degenerative disease or tissue injury, by administering to a subject in need of such treatment, a composition containing a therapeutically effective amount of a synthetic peptide of the present disclosure.

8 Claims, 12 Drawing Sheets
Specification includes a Sequence Listing.

```
SEQUENCE LISTING

<160> NUMBER OF SEQ ID NOS: 26

<210> SEQ ID NO 1
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 1
<223> OTHER INFORMATION: Xaa is Ser or Ala
<220> FEATURE:
<221> NAME/KEY: VARIANT
<222> LOCATION: 2
<223> OTHER INFORMATION: Xaa is Leu, Ala or Ile
<220> FEATURE:
<221> NAME/KEY: VARIANT
<222> LOCATION: 3
<223> OTHER INFORMATION: Xaa is Gly, Ala, Val or Asn
<220> FEATURE:
<221> NAME/KEY: VARIANT
<222> LOCATION: 4
<223> OTHER INFORMATION: Xaa is Ala, Gly or Glu
<220> FEATURE:
<221> NAME/KEY: VARIANT
<222> LOCATION: 6
<223> OTHER INFORMATION: Xaa is Gln, Ala or Asn

<400> SEQUENCE: 1

Xaa Xaa Xaa Xaa Glu Xaa
1               5

<210> SEQ ID NO 2
<211> LENGTH: 13
<212> TYPE: PRT
<213> ORGANISM: Artificial Sequence
<220> FEATURE:
<223> OTHER INFORMATION: synthetic;13-mer-dS

<400> SEQUENCE: 2

Ser Leu Gly Ala Glu Gln Arg Thr Glu Ser Ile Ile His
1               5                   10

<210> SEQ ID NO 3
<211> LENGTH: 12
<212> TYPE: PRT
<213> ORGANISM: Artificial Sequence
<220> FEATURE:
<223> OTHER INFORMATION: synthetic;12-mer-dS

<400> SEQUENCE: 3

Ser Leu Gly Ala Glu Gln Arg Thr Glu Ser Ile Ile
1               5                   10
```

```
<210> SEQ ID NO 4
<211> LENGTH: 11
<212> TYPE: PRT
<213> ORGANISM: Artificial Sequence
<220> FEATURE:
<223> OTHER INFORMATION: synthetic;11-mer-dS

<400> SEQUENCE: 4

Ser Leu Gly Ala Glu Gln Arg Thr Glu Ser Ile
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthetic;10-mer-dS

<400> SEQUENCE: 5

Ser Leu Gly Ala Glu Gln Arg Thr Glu Ser
1               5                   10

<210> SEQ ID NO 6
<211> LENGTH: 9
<212> TYPE: PRT
<213> ORGANISM: Artificial Sequence
<220> FEATURE:
<223> OTHER INFORMATION: synthetic;9-mer-dS

<400> SEQUENCE: 6

Ser Leu Gly Ala Glu Gln Arg Thr Glu
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic;8-mer-dS

<400> SEQUENCE: 7

Ser Leu Gly Ala Glu Gln Arg Thr
1               5

<210> SEQ ID NO 8
<211> LENGTH: 7
<212> TYPE: PRT
<213> ORGANISM: Artificial Sequence
<220> FEATURE:
<223> OTHER INFORMATION: synthetic;7-mer-dS

<400> SEQUENCE: 8

Ser Leu Gly Ala Glu Gln Arg
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic;6-mer-dS

<400> SEQUENCE: 9

Ser Leu Gly Ala Glu Gln
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: synthetic;5-mer-dS

<400> SEQUENCE: 10

Ser Leu Gly Ala Glu
1               5

<210> SEQ ID NO 11
<211> LENGTH: 4
<212> TYPE: PRT
<213> ORGANISM: Artificial Sequence
<220> FEATURE:
<223> OTHER INFORMATION: synthetic;4-mer-dS

<400> SEQUENCE: 11

Ser Leu Gly Ala
1

<210> SEQ ID NO 12
<211> LENGTH: 6
<212> TYPE: PRT
<213> ORGANISM: Artificial Sequence
<220> FEATURE:
<223> OTHER INFORMATION: synthetic;6-mer Sa

<400> SEQUENCE: 12

Ala Leu Gly Ala Glu Gln
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic;6-mer La

<400> SEQUENCE: 13

Ser Ala Gly Ala Glu Gln
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic;6-mer Ga

<400> SEQUENCE: 14

Ser Leu Ala Ala Glu Gln
1               5

<210> SEQ ID NO 15
<211> LENGTH: 6
<212> TYPE: PRT
<213> ORGANISM: Artificial Sequence
<220> FEATURE:
<223> OTHER INFORMATION: synthetic;6-mer Ag

<400> SEQUENCE: 15

Ser Leu Gly Gly Glu Gln
1               5

<210> SEQ ID NO 16
```

```
<211> LENGTH: 6
<212> TYPE: PRT
<213> ORGANISM: Artificial Sequence
<220> FEATURE:
<223> OTHER INFORMATION: synthetic;6-mer Ea

<400> SEQUENCE: 16

Ser Leu Gly Ala Ala Gln
1               5

<210> SEQ ID NO 17
<211> LENGTH: 6
<212> TYPE: PRT
<213> ORGANISM: Artificial Sequence
<220> FEATURE:
<223> OTHER INFORMATION: synthetic;6-mer Qa

<400> SEQUENCE: 17

Ser Leu Gly Ala Glu Ala
1               5

<210> SEQ ID NO 18
<211> LENGTH: 6
<212> TYPE: PRT
<213> ORGANISM: Artificial Sequence
<220> FEATURE:
<223> OTHER INFORMATION: synthetic;6-mer St

<400> SEQUENCE: 18

Thr Leu Gly Ala Glu Gln
1               5

<210> SEQ ID NO 19
<211> LENGTH: 6
<212> TYPE: PRT
<213> ORGANISM: Artificial Sequence
<220> FEATURE:
<223> OTHER INFORMATION: synthetic;6-mer Li

<400> SEQUENCE: 19

Ser Ile Gly Ala Glu Gln
1               5

<210> SEQ ID NO 20
<211> LENGTH: 6
<212> TYPE: PRT
<213> ORGANISM: Artificial Sequence
<220> FEATURE:
<223> OTHER INFORMATION: synthetic;6-mer Gv

<400> SEQUENCE: 20

Ser Leu Val Ala Glu Gln
1               5

<210> SEQ ID NO 21
<211> LENGTH: 6
<212> TYPE: PRT
<213> ORGANISM: Artificial Sequence
<220> FEATURE:
<223> OTHER INFORMATION: synthetic;6-mer Gn

<400> SEQUENCE: 21

Ser Leu Asn Ala Glu Gln
1               5

<210> SEQ ID NO 22
<211> LENGTH: 6
```

```
<212> TYPE: PRT
<213> ORGANISM: Artificial Sequence
<220> FEATURE:
<223> OTHER INFORMATION: synthetic;6-mer Ae

<400> SEQUENCE: 22

Ser Leu Gly Glu Glu Gln
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic;6-mer Ai

<400> SEQUENCE: 23

Ser Leu Gly Ile Glu Gln
1               5

<210> SEQ ID NO 24
<211> LENGTH: 6
<212> TYPE: PRT
<213> ORGANISM: Artificial Sequence
<220> FEATURE:
<223> OTHER INFORMATION: synthetic;6-mer As

<400> SEQUENCE: 24

Ser Leu Gly Ser Glu Gln
1               5

<210> SEQ ID NO 25
<211> LENGTH: 6
<212> TYPE: PRT
<213> ORGANISM: Artificial Sequence
<220> FEATURE:
<223> OTHER INFORMATION: synthetic;6-mer Ed

<400> SEQUENCE: 25

Ser Leu Gly Ala Asp Gln
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic;6-mer Qn

<400> SEQUENCE: 26

Ser Leu Gly Ala Glu Asn
1               5
```

SHORT SYNTHETIC PEPTIDES AND THEIR USES FOR TREATING RETINAL DEGENERATIVE DISEASES AND/OR TISSUE INJURIES

This application is a national stage filing under 35 U.S.C. 371 of International Application PCT/CN2019/102739, filed Aug. 27, 2019, the content of which is hereby incorporated by reference herein.

BACKGROUND OF THE INVENTION

1. Field of the Invention

The present disclosure relates to the discovery of short synthetic peptides having neuroprotective actions, and/or tissue repair and regenerating actions, thus are useful in the field of the treatment or prophylaxis of retinal degenerative diseases or tissue injuries.

2. Description of Related Art

Retinal degeneration is the deterioration of the retina caused by the progressive and eventual death of the retinal or retinal pigment ephitelium (RPE) cells. There are several reasons for retinal degeneration, including artery or vein occlusion, diabetic retinopathy, retrolental fibroplasia/retinopathy of prematurity, or disease (usually hereditary). These may present in many different ways such as impaired vision, night blindness, retinal detachment, light sensitivity, tunnel vision, and loss of peripheral vision to total loss of vision. Retinal degeneration is found in many different forms of retinal diseases including retinitis pigmentosa (RP), age-related macular degeneration (AMD), diabetic retinopathy, cataracts, acute UV retinopathy, and glaucoma.

Injuries to soft tissue, for example, vascular, skin, or musculoskeletal tissue, are quite common. Soft tissue conditions may include, for example, conditions of skin (e.g., ischemic wounds, diabetic wounds, traumatic wounds, burns, skin ulcers, and surgical wounds); vascular conditions (e.g., vascular disease, vascular injury, and improper vascular development); cosmetic conditions (e.g., those involving repair, augmentation, or beautification); muscle diseases (e.g., inflammatory, neurogenic, and myogenic muscle diseases; and muscular dystrophies); and conditions of connective tissues such as tendons and ligaments. Another soft tissue condition is skin aging or exposure to stress (e.g., UV exposure, pollution and etc), which causes tissue repair and cell regeneration to slow down. The skin aging process is marked by very distinct signs: the appearance of wrinkles, a variation in the skin pigmentation, loss of elasticity and compactness, and the relaxing of the tissues.

Accordingly, there exists a need in the related field an improved medication and/or method for treating and/or preventing retinal degenerative diseases and/or a condition that requires tissue repair and regeneration.

SUMMARY OF THE INVENTION

In general, the present disclosure relates to the development of novel compounds and/or methods for treating a retinal degenerative disease and/or a tissue injury.

Accordingly, the first aspect of the present disclosure aims at providing a short synthetic peptide capable of treating a retinal degenerative disease or tissue injury. The short synthetic peptide consists of the amino acid sequence set forth as $X_1X_2X_3X_4EX_5$ (SEQ ID NO: 1), wherein, $X_1$ is serine (S), or alanine (A);
$X_2$ is leucine (L), alanine (A) or isoleucine (I);
$X_3$ is glycine (G), alanine (A), valine (V) or asparagine (N);
$X_4$ is alanine (A), glycine (G) or glutamic acid (E);
$X_5$ is glutamine (Q), alanine (A) or asparagine (N); and
$X_2$, $X_3$, $X_4$, and $X_5$ are independently in L-form, while $X_1$ and E are independently in L- or D-form; and
in the case when the SEQ ID NO: 1 has the sequence of SLGAEQ (SEQ ID NO: 9), then the serine (S) or the glutamic acid (E) is in D-form.

According to optional embodiments, the N-terminus of the amino acid sequence of the synthetic peptide is acetylated and the C-terminus of the amino acid sequence is amidated.

According to some embodiments, $X_1$ is serine (S), $X_2$ is leucine (L), $X_3$ is glycine (G), $X_4$ is alanine (A), $X_5$ is glutamine (Q), and the synthetic peptide has the amino acid sequence of SLGAEQ (SEQ ID NO: 9, hereinafter "6-mer").

According to other preferred embodiments, the synthetic peptide has the amino acid sequence that is any of SEQ ID NOs: 12, 13, 14, 15, 17, 19, 20, 21, 22, or 26. In one example, $X_1$ is alanine (A), $X_2$ is leucine (L), $X_3$ is glycine (G), $X_4$ is alanine (A), $X_5$ is glutamine (Q), and the synthetic peptide has the amino acid sequence of SEQ ID NO:12 (hereinafter "6-mer Sa"). In another example, $X_1$ is serine (S), $X_2$ is alanine (A), $X_3$ is glycine (G), $X_4$ is alanine (A), $X_5$ is glutamine (Q), and the synthetic peptide has the amino acid sequence of SEQ ID NO: 13 (hereinafter "6-mer La"). In yet another example, $X_1$ is serine (S), $X_2$ is leucine (L), $X_3$ and $X_4$ are independently alanine (A), $X_5$ is glutamine (Q), and the synthetic peptide has the amino acid sequence of SEQ ID NO: 14 (hereinafter "6-mer Ga"). In yet another example, $X_1$ is serine (S), $X_2$ is leucine (L), $X_3$ is glycine (G), $X_4$ is glycine (G), $X_5$ is glutamine (Q), and the synthetic peptide has the amino acid sequence of SEQ ID NO:15 (hereinafter "6-mer Ag"). In yet another example, $X_1$ is serine (S), $X_2$ is leucine (L), $X_3$ is glycine (G), $X_4$ and $X_5$ are independently alanine (A), and the synthetic peptide has the amino acid sequence of SEQ ID NO: 17 (hereinafter "6-mer Qa"). In a further example, $X_1$ is serine (S), $X_2$ is isoleucine (I), $X_3$ is glycine (G), $X_4$ is alanine (A), $X_5$ is glutamine (Q), and the synthetic peptide has the amino acid sequence of SEQ ID NO: 19 (hereinafter "6-mer Li"). In another example, $X_1$ is serine (S), $X_2$ is leucine (L), $X_3$ is valine (V), $X_4$ is alanine (A), $X_5$ is glutamine (Q), and the synthetic peptide has the amino acid sequence of SEQ ID NO: 20 (hereinafter "6-mer Gv"). In yet another example, $X_1$ is serine (S), $X_2$ is leucine (L), $X_3$ is asparagine (N), $X_4$ is alanine (A), $X_5$ is glutamine (Q), and the synthetic peptide has the amino acid sequence of SEQ ID NO: 21 (hereinafter "6-mer Gn"). In yet another example, $X_1$ is serine (S), $X_2$ is leucine (L), $X_3$ is glycine (G), $X_4$ is glutamic acid (E), $X_5$ is glutamine (Q), and the synthetic peptide has the amino acid sequence of SEQ ID NO: 22 (hereinafter "6-mer Ae"). In a further example, $X_1$ is serine (S), $X_2$ is leucine (L), $X_3$ is glycine (G), $X_4$ is alanine (A), $X_5$ is asparagine (N), and the synthetic peptide has the amino acid sequence of SEQ ID NO: 26 (hereinafter "6-mer Qn").

In further examples, $X_1$ and glutamic acid (E) of the 6-mer are independently in L- or D-form, while the rest of the amino acid residues are all in L-form. In one example, $X_1$ of the 6-mer is D-form alanine (hereinafter "6-mer dS"). In a further example, glutamine (Q) of the 6-mer is in D-form (hereafter "6-mer dE").

The second aspect of the present disclosure aims at providing a medicament and/or a composition suitable for treating a retinal degenerative disease or a tissue injury. The medicament or composition comprises, an effective amount of the synthetic peptide described above, and a pharmaceutically acceptable carrier.

According to some preferred embodiments, the synthetic peptide has the amino acid sequence of SEQ ID NO: 9 (hereinafter 6-mer). According to other preferred embodiments, the synthetic peptide has the amino acid sequence that is any of SEQ ID NOs: 12, 13, 14, 15, 17, 19, 20, 21, 22 or 26. In one example, the synthetic peptide has the amino acid sequence of SEQ ID NO: 12 (hereinafter "6-mer Sa"). In another example, the synthetic peptide has the amino acid sequence of SEQ ID NO: 13 (hereinafter "6-mer La"). In another example, the synthetic peptide has the amino acid sequence of SEQ ID NO: 14 (hereinafter "6-mer Ga"). In another example, the synthetic peptide has the amino acid sequence of SEQ ID NO: 15 (hereinafter "6-mer Ag"). In a further example, the synthetic peptide has the amino acid sequence of SEQ ID NO: 17 (hereinafter "6-mer Qa"). In a further example, the synthetic peptide has the amino acid sequence of SEQ ID NO: 19 (hereinafter "6-mer Li"). In another example, the synthetic peptide has the amino acid sequence of SEQ ID NO: 20 (hereinafter "6-mer Gv"). In still another example, the synthetic peptide has the amino acid sequence of SEQ ID NO: 21 (hereinafter "6-mer Gn"). In a further example, the synthetic peptide has the amino acid sequence of SEQ ID NO: 22 (hereinafter "6-mer Ae"). In still a further example, the synthetic peptide has the amino acid sequence of SEQ ID NO: 26 (hereinafter "6-mer Qn").

In some embodiments, the 6-mer synthetic peptide (SEQ ID NO: 9) has at least one D-form amino acid residue. Preferably, the second, third, fourth, and sixth residues of the 6-mer are independently in L-form, while the first and the fifth amino acid residues are in L- or D-form. In one example, the first residue of the 6-mer is D-form alanine (6-mer dS). In another example, the fifth residue of the 6-mer is D-form glutamic acid (6-mer dE).

The retinal degenerative disease treatable by the present medicament or composition is any of diabetic retinopathy, diabetic macular edema, age-related macular degeneration (AMD), retinitis pigmentosa (RP), cataracts, glaucoma, or acute UV retinopathy.

The tissue injury treatable by the present medicament or composition is dry eye disease (DED) or retinal ischemia/reperfusion injury.

The medicament or composition of the present disclosure may be administered to the subject via intravascular delivery (e.g., injection or infusion), oral, enteral, rectal, pulmonary (e.g., inhalation), nasal, topical (including transdermal, buccal and sublingual), intravesical, intravitreal, subconjunctival, intraperitoneal, vaginal, brain delivery (e.g., intra-cerebroventricular, and intracerebral), CNS delivery (e.g., intrathccal, perispinal, and intra-spinal) or parenteral (e.g., subcutaneous, intramuscular, intravenous, and intradermal), transmucosal administration or administration via an implant, or other delivery routes known in the art.

The third aspect of the present disclosure is thus directed to a method of treating a subject suffering from a retinal degenerative disease or a tissue injury. The method comprises the step of, administering to the subject a medicament or a composition of the present disclosure described above for ameliorating or alleviating symptoms related to the retinal degenerative disease or the tissue injury In all embodiments, the subject is a human.

In preferred embodiments, the synthetic peptide of the present disclosure is administered in an amount of 0.001-100 mg/Kg to the subject.

The details of one or more embodiments of the invention are set forth in the accompanying description below. Other features and advantages of the invention will be apparent from the detail descriptions, and from claims.

BRIEF DESCRIPTION OF THE DRAWINGS

The present description will be better understood from the following detailed description read in light of the accompanying drawings, where.

In the control group and the 6-mer dS plus I/R group, the GCL and the INL were clear and well organized. Original magnification×200.

Figure 9:
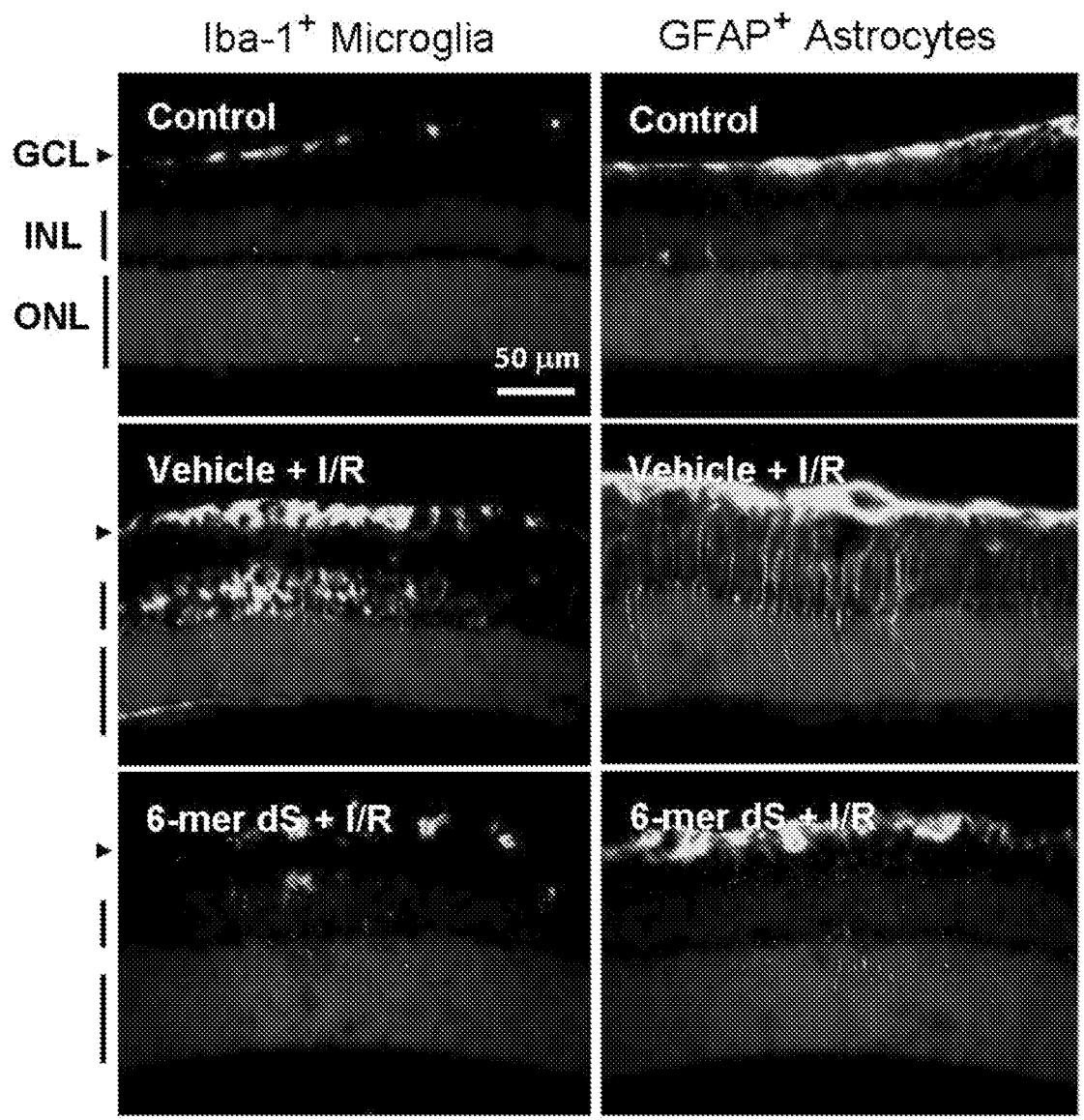

FIG. 9. Representative images of microglia and astrocytes immunostaining patterns in non-ischemic (control) and ischemic retinas 2 weeks after I/R injury. The retinal sections were stained with Iba-1 (green; a microglia marker), GFAP (green; a astrocyte marker) and Hoechst 33258 (blue). Representative graphs were from three independent experiments and obtained at 400×magnification.

Figure 10:
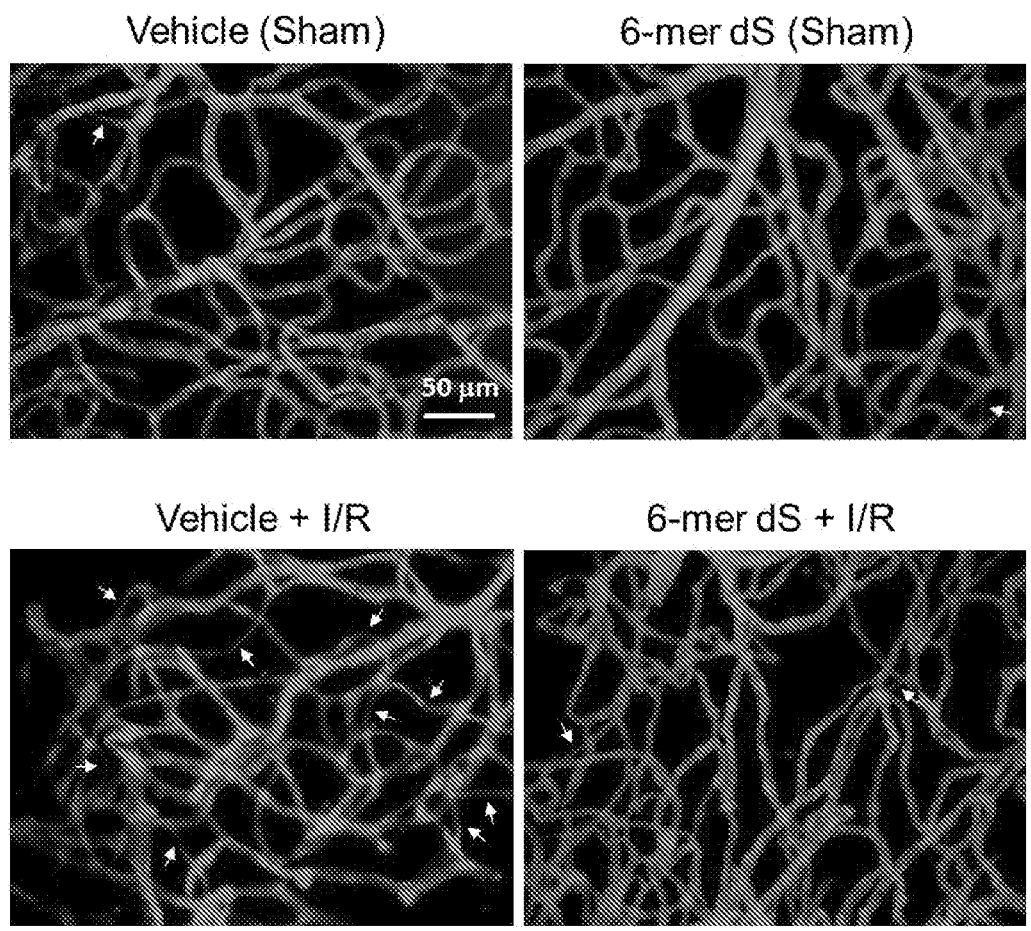

FIG. 10. Representative images of the degenerate capillaries in contralateral eye (sham) and ischemic retinas at 2 weeks after I/R injury. The rat retinal microvasculature was stained with isolectin GS-IB4 (red) and counterstaining with Hoechst 33258 (blue; pericyte nuclei staining). Arrows: degenerate capillary with thin tubes and nonuclei. The experiments were from three independent experiments. Original magnification×400.

Figure 11:
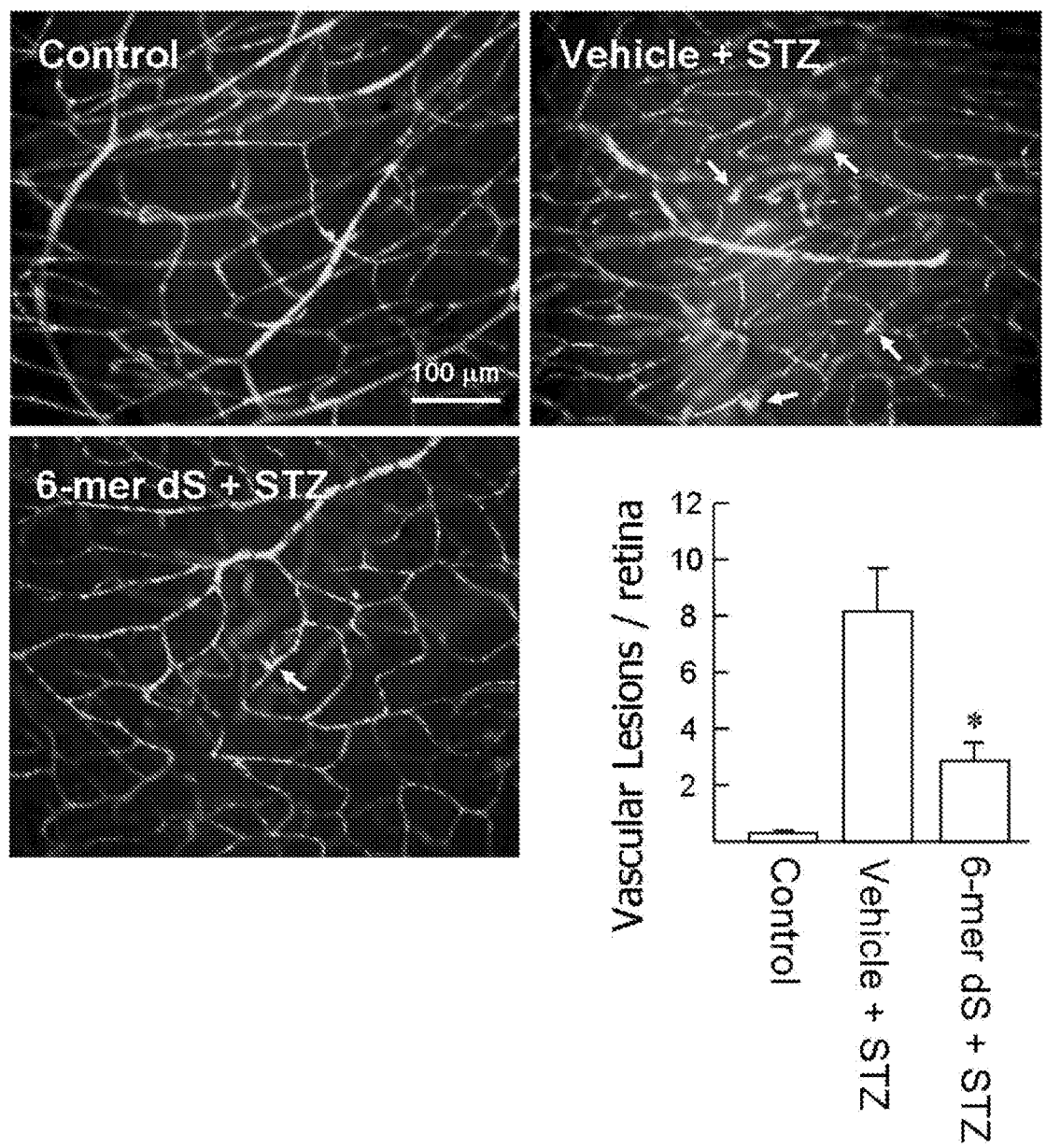

FIG. 11. Representative fluorescent images of the flat mounted retina from diabetic mice treated with vehicle or 6-mer dS eye drop at week 2 after STZ injection. Vascular permeability was determined by intraperitoneal injection of FITC-BSA. The arrows point the vascular hemorrhaging lesions with accumulated FITC-BSA in the retinas. The numbers of hemorrhaging areas in a retina, expressed as mean±SD (n=6 per group). Original magnification ×200. *P<0.007 versus vehicle/STZ group.

Figure 12:
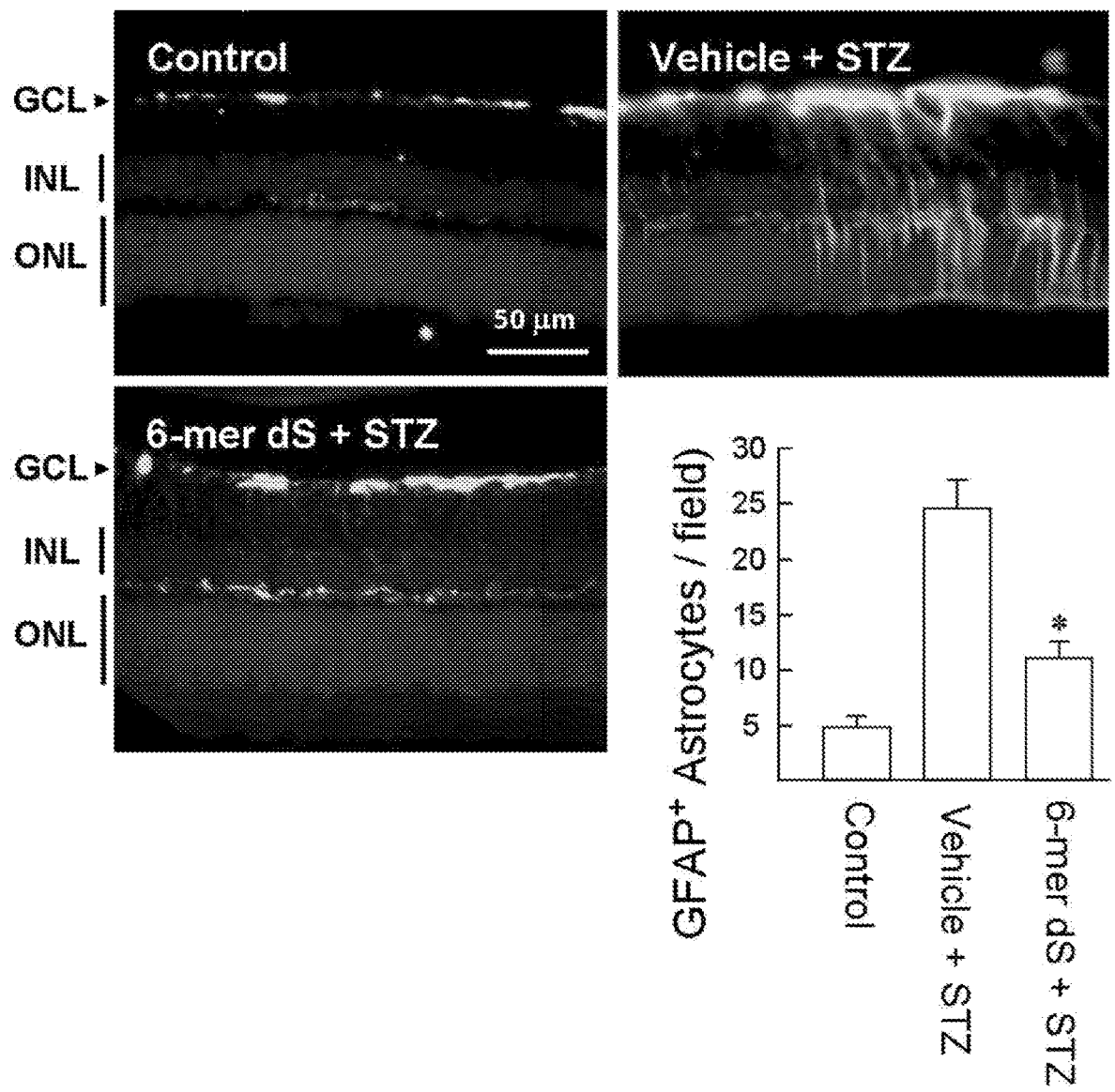

FIG. 12. Representative fluorescent images of GFAP-positive astrocytes in retina from sham control and diabetic mice treated with vehicle or 6-mer dS eye drop at week 2 after STZ injection. Data from three independent experiments (n=6 per group). Original magnification×400. *P<0.0002 versus vehicle/STZ group.

Figure 13:
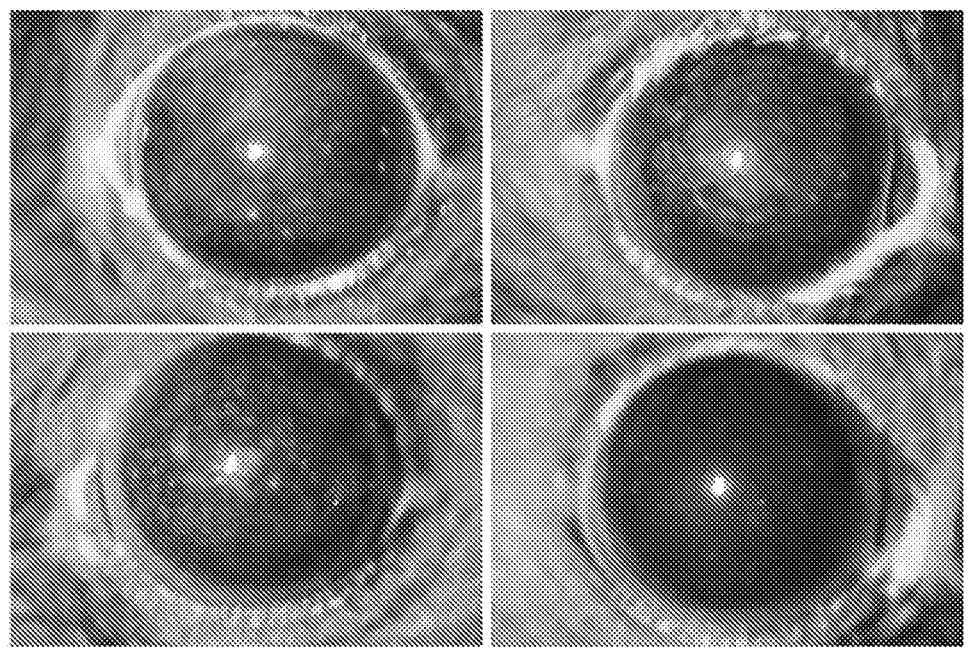
Figure 13:
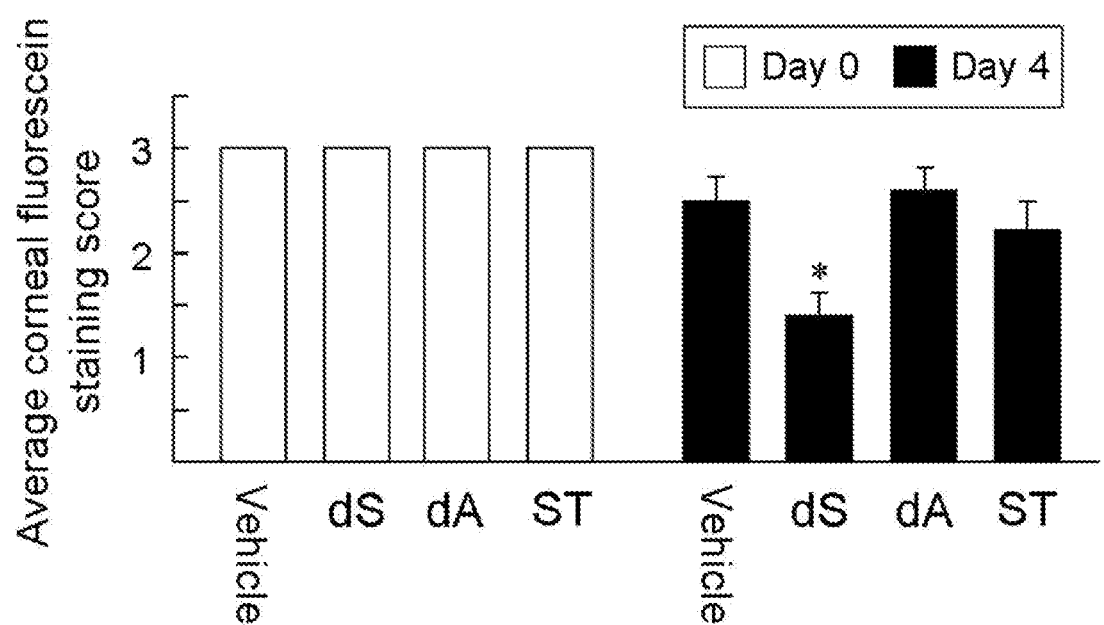

FIG. 13. The effect of 6-mer variant peptides on corneal epithelial injury. C57BL6 mice were housed at controlled environment chamber (CEC) for 14 days to induce ocular surface disruption (Day 0) and then treatment of the dry eye with the 6-mer variant peptide or vehicle for further 4 days (Day 4). (A) Representative corneal fluorescein-stained images from the mice at day 0 and at day 4. (B) Scoring of corneal epithelial damage as judged by the degrees of fluorescein staining. Values are expressed as mean±SD in each group (n=10). *P<0.000001 versus 6-mer dS group at day 0.

Figure 14:
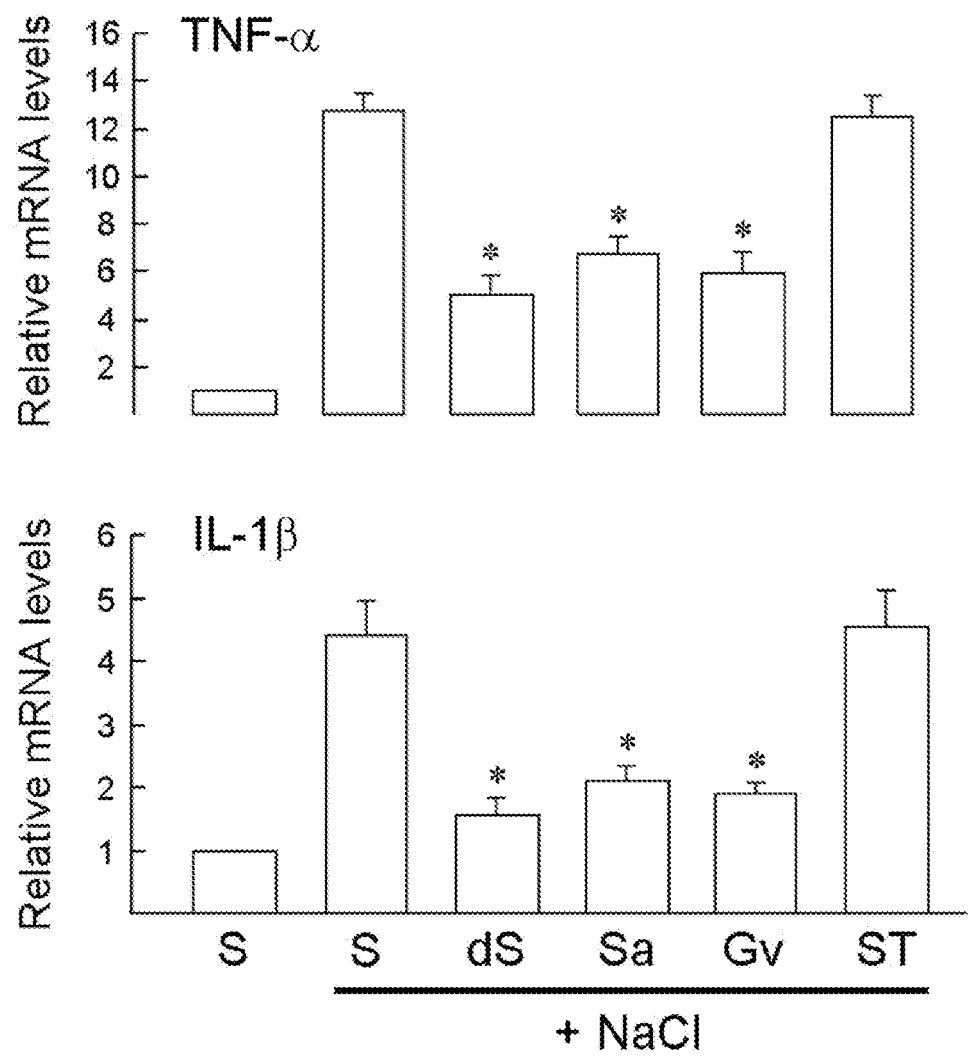

FIG. 14. The effects of 6-mer variant peptides on proinflammatory gene expression induced by hyperosmotic stress in rabbit corneal epithelial cells. Three independent assays are performed and data are represented as the mean±SD. *P<0.003 versus solvent control.

DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. DEFINITIONS

For convenience, certain terms employed in the context of the present disclosure are collected here. Unless defined otherwise, all technical and scientific terms used herein have the same meaning as commonly understood by one of the ordinary skill in the art to which this invention belongs.

As used herein, the term "peptide" denotes a polymer of amino acid residues. By the term "synthetic peptide" as used herein, it is meant a peptide which does not comprise an entire naturally occurring protein molecule. The peptide is "synthetic" in that it may be produced by human intervention using such techniques as chemical synthesis, recombinant genetic techniques, or fragmentation of whole antigen or the like. Throughout the present disclosure, the positions of any specified amino acid residues within a peptide are numbered starting from the N terminus of the peptide. When amino acids are not designated as either D- or L-amino acids, the amino acid is either an L-amino acid or could be either a D- or L-amino acid, unless the context requires a particular isomer. Further, the notation used herein for the polypeptide amino acid residues are those abbreviations commonly used in the art.

As discussed herein, minor variations in the amino acid sequences of proteins/peptides are contemplated as being encompassed by the presently disclosed and claimed inventive concept(s), providing that the variations in the amino acid sequence maintain at least 90%, such as at least 70%, 71%, 72%, 73%, 75%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99%. The present synthetic peptide may be modified specifically to alter a feature of the peptide unrelated to its physiological activity. For example, certain amino acids can be changed and/or deleted without affecting the physiological activity of the peptide in this study (i.e., its ability to treat angiogenesis related diseases and/or conditions). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of proteins/peptides can be readily prepared by those of ordinary skill in the art. Preferred amino- and carboxy-termini of fragments or analogs occur near boundaries of functional domains. In one example, one amino acid residue (e.g., aspartate, valine or phenylalanine) of the present synthetic peptide is conservatively replaced by non-polar amino acid residue (e.g., by alanine) In other examples, one amino acid residue of the present synthetic peptide is conservatively replaced by its D-form amino acid residue, for example, L-form serine (S) and L-form glutamic acid (E) are respectively replaced by the corresponding D-form residues.

The term "treatment" as used herein are intended to mean obtaining a desired pharmacological and/or physiologic effect, e.g., neuroprotective effect or promoting tissue repair or regeneration. The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., retinal degeneration or tissue injury) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "administered", "administering" or "administration" are used interchangeably herein to refer a mode of delivery, including, without limitation, intraveneously, intramuscularly, intraperitoneally, intraarterially, intracranially, or subcutaneously administering an agent (e.g., a compound or a composition) of the present invention. In some embodiments, the synthetic peptide of the present disclosure and/or its analogues are formulated into eye drops for direct application on the corneal surface. In other embodiments, the synthetic peptide of the present disclosure and/or its analogues are formulated into skin ointments or lotions for direct application on the skin. In further embodiments, the synthetic peptide of the present disclosure and/or its analogues are formulated into powders for mixed with suitable carrier (e.g., buffer solution) before use, such as intraveneous injection.

The term "an effective amount" as used herein refers to an amount effective, at dosages, and for periods of time necessary, to achieve the desired result with respect to the treatment of a disease. For example, in the treatment of a retinal degenerative disease, an agent (i.e., a compound, a synthetic peptide, or a nucleic acid encoding a therapeutic peptide) which decrease, prevents, delays or suppresses or arrests any symptoms of the retinal degenerative disease would be effective. Similarly, in the treatment of a condition in need of tissue repair or regeneration, an agent (i.e., a compound, a synthetic peptide, or a nucleic acid encoding a therapeutic peptide) which decrease, prevents, delays or suppresses or arrests any symptoms of the condition or promotes tissue repair or regeneration would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

The term "subject" or "patient" is used interchangeably herein and is intended to mean a mammal including the human species that is treatable by the synthetic peptide and/or method of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. DETAIL DESCRIPTION OF PREFERRED EMBODIMENTS

The present disclosure is based, at least in part, on the discovery of short synthetic peptides that are capable of treating and/or preventing a subject from developing retinal degenerative disease or tissue injury. Accordingly, this invention provides method and composition comprising the newly identified synthetic peptides for the treatment and/or prophylaxis of a retinal degenerative disease or tissue injury.

2.1 The present synthetic peptides

The short synthetic peptide of the present disclosure consists of the amino acid sequence set forth as $X_1X_2X_3X_4X_5$ (SEQ ID NO: 1), wherein,
  $X_1$ is serine (S), or alanine (A);
  $X_2$ is leucine (L), alanine (A) or isoleucine (I);
  $X_3$ is glycine (G), alanine (A) or valine (V) or asparagine (N);
  $X_4$ is alanine (A), glycine (G) or glutamic acid (E);
  $X_5$ is glutamine (Q), alanine (A) or asparagine (N); and
  $X_2$, $X_3$, $X_4$, and $X_5$ are independently in L-form, while $X_1$ and E are independently in L- or D-form; and
  in the case when the SEQ ID NO: 1 has the sequence of SLGAEQ (SEQ ID NO: 9), then the serine (S) or the glutamic acid (E) is in D-form.

Alternatively or optionally, the N-terminus of the amino acid sequence of the synthetic peptide is acetylated and the C-terminus of the amino acid sequence is amidated.

According to one preferred embodiment, the synthetic peptide of the present disclosure has the amino acid sequence of SLGAEQ (SEQ ID NO: 9, 6-mer). Preferably, the 6-mer synthetic peptide includes at least one D-form amino acid residues therein, and thereby give rise to its D-form analogues. In one preferred embodiment, the serine residue in the 6-mer peptide is in D-form (6-mer dS). In another preferred embodiment, the glutamic acid residue in the 6-mer peptide is in D-form (6-mer dE).

According to other embodiments, the 6-mer synthetic peptide may have a conservative substitution therein, thereby give rise to an analogue having the amino acid sequence that is any of SEQ ID Nos: 12, 13, 14, 15, 17, 19, 20, 21, 22, or 26.

The present synthetic peptides are described in detail in Table 1 below.

TABLE 1

The present synthetic peptides

| Peptide Name | Amino Acid Sequence | SEQ ID NO |
|---|---|---|
| 6-mer | NH$_2$-Ser-Leu-Gly-Ala-Glu-Gln-COOH SLGAEQ | 9 |
| *6-mer variants* | | |
| 6-mer Sa | NH$_2$-Ala-Leu-Gly-Ala-Glu-Gln-COOH ALGAEQ | 12 |
| 6-mer La | NH$_2$-Ser-Ala-Gly-Ala-Glu-Gln-COOH SAGAEQ | 13 |
| 6-mer Ga | NH$_2$-Ser-Leu-Ala-Ala-Glu-Gln-COOH SLAAEQ | 14 |
| 6-mer Ag | NH$_2$-Ser-Leu-Gly-Gly-Glu-Gln-COOH SLGGEQ | 15 |
| 6-mer Qa | NH$_2$-Ser-Leu-Gly-Ala-Glu-Ala-COOH SLGAEA | 17 |
| 6-mer Li | NH$_2$-Ser-Ile-Gly-Ala-Glu-Gln-COOH SIGAEQ | 19 |
| 6-mer Gv | NH$_2$-Ser-Leu-Val-Ala-Glu-Gln-COOH SLVAEQ | 20 |
| 6-mer Gn | NH$_2$-Ser-Leu-Asn-Ala-Glu-Gln-COOH SLNAEQ | 21 |
| 6-mer Ae | NH$_2$-Ser-Leu-Gly-Glu-Glu-Gle-COOH SLGEEQ | 22 |
| 6-mer Qn | NH$_2$-Ser-Leu-Gly-Ala-Glu-Asn-COOH SLGAEN | 26 |
| *6-mer D form analogues* | | |
| 6-mer dS | NH$_2$-(D-Ser)-Leu-Gly-Ala-Glu-Gln-COOH SLGAEQ | 9 |
| 6-mer dE | NH$_2$-Ser-Leu-Gly-Ala-(D-Glu)-Gln-COOH SLGAEQ | 9 |

The bold letter in any sequence indicates that particular amino acid is in D-form.

According to preferred embodiments, the sixth amino acid residue (i.e., glutamine (Q)) of the 6-mer (SEQ ID NO: 9) must be present, or else the synthetic peptide will lose its neuroprotective activity. In one embodiment, a 5-mer synthetic peptide (SEQ ID NO: 10) is produced, in which the sixth amino acid residue (Q) from the 6-mer is deleted, and the 5-mer lacks any significant neuroprotective activity.

According to other embodiments, the first, second, third, fourth and sixth amino acid residues of the 6-mer (SEQ ID NO: 9) may be independently substituted with other conservative amino acid residues. In one embodiment, the first residue (i.e., serine (S)) of the 6-mer is replaced by alanine (A), thereby gives rise to the synthetic peptide of the amino acid sequence of SEQ ID NO: 12 (hereinafter "6-mer Sa"). In another embodiment, the second residue (i.e., leucine (L)) of the 6-mer is replaced by alanine (A), thereby gives rise to the synthetic peptide of the amino acid sequence of SEQ ID NO: 13 (hereinafter "6-mer La"). Alternatively, the leucine (L) residue of the 6-mer is replaced by isoleucine (I), thereby gives rise to the synthetic peptide of the amino acid sequence of SEQ ID NO: 19 (hereinafter "6-mer Li"). In still another embodiment, the third residue (i.e., glycine (G)) of the 6-mer is replaced by alanine (A), thereby gives rise to the synthetic peptide of the amino acid sequence of SEQ ID NO: 14 (hereinafter "6-mer Ga"). Alternatively, the glycine (G) residue of the 6-mer is replaced by valine (V), thereby gives rise to the synthetic peptide of the amino acid sequence of SEQ ID NO: 20 (hereinafter "6-mer Gv"). In still another embodiment, the fourth residue (i.e., alanine (A)) of the 6-mer is replaced by glycine (G), thereby gives rise to the synthetic peptide of the amino acid sequence of SEQ ID NO: 15 (hereinafter "6-mer Ag"). Alternatively, the alanine (A) residue of the 6-mer is replaced by glutamic acid (E), and the synthetic peptide has the amino acid sequence of SEQ ID NO: 22 (hereinafter "6-mer Ae"). In a further embodiment, the sixth residue (i.e., glutamine (Q)) of the 6-mer is replaced by alanine (A), thereby give rise to the synthetic peptide of the amino acid sequence of SEQ ID NO: 17 (hereinafter "6-mer Qa"). Alternatively, the glutamine (Q) residue of the 6-mer is replaced by asparagine (N), and the synthetic peptide has the amino acid sequence of SEQ ID NO: 26 (hereinafter "6-mer Qn").

According to further embodiments, at least one D-form amino acid residues is included in the 6-mer synthetic peptide, particularly, each of the amino acid residues at positions 2, 3, 4 and 6 of the 6-mer must remain in L-form, while the first and fifth positions of the 6-mer may be in L- or D-form. In some embodiments, the amino acid residues at positions 1 and 5 of the 6-mer are independently in D-forms, thus give rises to D-form analogues of the 6-mer as described in Table 1 above.

The present synthetic peptide may be synthesized in accordance with any standard peptide synthesis protocol in the art. For example, the present synthetic peptides may be synthesized by use of a solid-phase peptide synthesizer (AB1433A peptide synthesizer, Applied Biosystems Inc., Life Technologies Corp., Foster City, CA, USA) in accordance with the manufacturer's protocols.

Alternatively, the present synthetic peptides may be prepared using recombinant technology. For example, one can clone a nucleic acid encoding the present peptide in an expression vector, in which the nucleic acid is operably linked to a regulatory sequence suitable for expressing the present peptide in a host cell. One can then introduce the vector into a suitable host cell to express the peptide. The expressed recombinant polypeptide can be purified from the host cell by methods such as ammonium sulfate precipitation and fractionation column chromatography. A peptide thus prepared can be tested for its activity according to the method described in the examples below.

The above-mentioned nucleic acids or polynucleotide can be delivered by the use of polymeric, biodegradable microparticle or microcapsule delivery devices known in the art. Another way to achieve uptake of the nucleic acid in a host is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

The present synthetic peptide may be modified at its N-terminus or C-terminus. Examples of N-terminal modifications include, but are not limited to, N-glycated, N-alkylated, and N-acetylated amino acid. A terminal modification can include a pegylation. An example of C-terminal modification is a C-terminal amidated amino acid. Alternatively, one or more peptide bond may be replaced by a non-peptidyl linkage, the individual amino acid moieties may be modified through treatment with agents capable of reacting with selected side chains or terminal residues.

Various functional groups may also be added at various points of the synthetic peptide that are susceptible to chemical modification. Functional groups may be added to the termini of the peptide. In some embodiments, the function groups improve the activity of the peptide with regard to one or more characteristics, such as improving the stability, efficacy, or selectivity of the synthetic peptide; improving the penetration of the synthetic peptide across cellular membranes and/or tissue barrier; improving tissue localization; reducing toxicity or clearance; and improving resistance to expulsion by cellular pump and the like. Non-limited examples of suitable functional groups are those that facilitate transport of a peptide attached thereto into a cell, for example, by reducing the hydrophilicity and increasing the lipophilicity of the peptide, these functional groups may optionally and preferably be cleaved in vivo, either by hydrolysis or enzymatically, inside the cell. Hydroxy protecting groups include esters, carbonates and carbamate protecting groups. Amine protecting groups include alkoxy and aryloxy carbonyl groups. Carboxylic acid protecting groups include aliphatic, benzylic and aryl esters.

A "peptidomimetic organic moiety" can optionally be substituted for amino acid residues in the present synthetic peptide both as conservative and as non-conservative substitutions. The peptidomimetic organic moieties optionally and preferably have steric, electronic or configuration properties similar to the replaced amino acid and such peptidomimetics are used to replace amino acids in the essential positions, and are considered conservative substitutions. Peptidomimetics may optionally be used to inhibit degradation of peptides by enzymatic or other degradative processes. The peptidomimetics can optionally and preferably be produced by organic synthetic techiniques. Non-limiting examples of suitable petidomimetics include isosteres of amide bonds, 3-amino-2-propenidone-6-carboxylic acid, hydroxyl-1,2,3,4-tetrahydro-isoquinoline-3-carboxylate, 1,2,3,4-tetrahydro-isoquinoline-3-carboxylate, and histidine isoquinolone carboxylic acid.

Any part of the synthetic peptide may optionally be chemically modified, such as by the addition of functional groups. The modification may optionally be performed during the synthesis of the present peptide. Non-limiting exemplary types of the modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxy groups to an amino group of a sugar. Acetal and ketal bonds can also optionally be formed between amino acids and carbonhydrates.

2.2 Compositions for the Treatment of a Retinal Degenerative Diseases and/or a Condition in Need of Tissue Repair or Regeneration The present synthetic peptides are suitable for treating a subject suffering from a retinal degenerative disease and/or a tissue injury, in which tissue repair or regeneration is required. Accordingly, a further aspect of the present disclosure is to provide a medicament comprising the present synthetic peptide for treating a retinal degenerative disease and/or a tissue injury.

In one embodiment, the medicament is for the treatment of a retinal degenerative disease, particularly, diabetic retinopathy, diabetic macular edema, age-related macular degeneration (AMD), retinitis pigmentosa (RP), glaucoma, or acute UV retinopathy.

In another embodiment, the medicament is for the treatment of a tissue injury, particularly, dry eye disease (DED) or retinal ischemia/reperfusion (I/R) injury.

The medicament is manufactured by mixing suitable amount of the present synthetic peptide with a pharmaceutically acceptable carrier, excipient or stabilizer into a composition. In particular embodiments, the synthetic peptide is selected from the group of peptides as described above, which include but are not limited to, 6-mer, 6-mer Sa, 6-mer La, 6-mer Ga, 6-mer Ag, 6-mer Qa, 6-mer Li, 6-mer Gv, 6-mer Gn, 6-mer Ae, 6-mer Qn, 6-mer dS, 6-mer dE, and a combination thereof.

The amount of the peptide present in the medicament or the composition will depend on the peptide used. The peptide typically will be present in the composition in the amount from about 0.001% to about 10% by weight, such as 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.9, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0% by weight; in particular in an amount from about 0.01% to about 5% by weight, such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.9, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0% by weight.

Pharmaceutical acceptable carriers, excipients or stabilizers for use with the synthetic peptides are well known in the relevant art, and include but are not limited to non-toxic inert solid, semi-solid, or liquid filler, diluent, encapsulating agent or formulation auxiliary. Typical pharmaceutically acceptable carrier is water or physiological saline. Examples of pharmaceutically acceptable carriers include, but are not limited to, sugars such as lactose, glucose, and sucrose; starches such as corn starch; cellulose and its derivatives such as carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; as well as other agents such as non-toxic lubricants (e.g., lauryl sulfate and magnesium stearate), coloring agents, releasing agents, flavoring agents, preservatives and antioxidants. The composition may further comprise an anti-biotic or an anti-mycotic agent therein.

Suitable routes of administration of the medicament or the composition of the present invention are intravascular delivery (e.g., injection or infusion), oral, enteral, rectal, pulmonary (e.g., inhalation), nasal, topical (including transdermal, buccal and sublingual), intravesical, intravitreal, intraperitoneal, vaginal, brain delivery (e.g., intracerebroventricular, and intracerebral), CNS delivery (e.g., intrathccal, perispinal, and intra-spinal) or parenteral (e.g., subcutaneous, intramuscular, intravenous, and intradermal), transmucosal administration or administration via an implant, or other delivery routes known in the art.

Pharmaceutical composition suitable for oral administration may be formulated into discrete dosage units such as pills, tablets, lozenges or hard or soft capsules, or as a dispersible powder or granules, or as a solutions or suspension for example, aqueous or oily suspensions, emulsions, syrups, elixirs, or enteral formulas. In one preferred example, the pharmaceutical composition is an eye drop. The composition may be presented in uni-dose or multi-dose containers, such as sealed vials or ampoules, and may be stored in a lyophilized condition requiring the addition of sterile liquid carrier (e.g., water or saline) prior to use.

Pharmaceutical composition suitable for parental administration may be formulated into aqueous or non-aqueous sterile injection by mixing or dispersing the present synthetic peptide with a sterile solvent, such as water, Ringer's solution, saline, 1,3-butanediol, alcohol and etc. Alternatively, fixed oil, fatty acid or synthetic mono- or diglycerides may be used as the solvent. The composition may be sterilized by filtering through a filter.

For topical or transdermal application, the pharmaceutical composition is generally formulated into ointments, pastes, creams, lotions, gels, patches or sprays. Ophthalmic formulations, ear drops, and eye drops are also contemplated within the scope of the invention. According to some embodiments, compositions of the invention are administered topically to the eye. According to other embodiments, the pharmaceutical composition is an ointment for skin use. Depending on the type and severity of the disease, about 1 μg/kg to about 100 mg/kg (e.g., 0.01-50 mg/kg) of the present synthetic peptide is administered to the patient, such as 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 900, 910, 920, 930, 940, 950, 960, 970, 980, 990, or 1,000 μg/kg; or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg. A typical daily or weekly dosage might range from about 0.01 mg/Kg to about 50 mg/kg or more, such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg/Kg. The doses utilized for any of the above-described purposes of topical administration will generally be administered one to several, e.g., four, six, eight or even more, times per day.

Pharmaceutical composition suitable for pulmonary administration is formulated as find dusts or mists which may be generated by means of metered dose pressurized aerosols, nebulisers or insufflators.

The pharmaceutical composition provided by the invention preferably is presented in the form of a kit. In the present invention, a "kit" is understood as a product containing the synthetic peptide(s) provided by the present invention and/or the additional therapeutic compounds forming the packaged composition such that the transport, storage and simultaneous or successive administration thereof is allowed. Therefore, the kits of the invention can contain one or more sealed ampoules respectively contain the synthetic peptides of the invention, and which can be prepared in a single dose or as multiple doses. The kit can additionally contain a vehicle suitable for solubilizing the synthetic peptides such as aqueous media such as saline solution, Ringer's solution, dextrose and sodium chloride; water-soluble media such as alcohol, polyethylene glycol, propylethylene glycol; and water-insoluble vehicles if necessary. Another component which may be present in the kit is a package which allows maintaining the compositions of the invention within determined limits. Materials suitable for preparing such packages include glass, plastic (polyethylene, polypropylene, polycarbonate and the like), bottles, vials, paper, sachets and the like.

The kit of the invention can additionally contain instructions for the simultaneous, successive or separate administration of the different formulations present in the kit. Therefore, the kit of the invention can further comprise instructions for the simultaneous, successive or separate administration of the different components. Said instructions can be in the form of printed material or in the form of an electronic support which can store the instructions such that they can be read by a subject, such as electronic storage media (magnetic disks, tapes and the like), optical media (CD-ROM, DVD) and the like. The media can additionally or alternatively contain Internet webpages providing said instructions.

2.3 Methods for the Treatment of a Retinal Degenerative Diseases and/or a Condition in need of Tissue Repair or Regeneration As it has been indicated above, the findings described in the present invention are useful for the prevention and/or treatment of a retinal degenerative diseases and/or a tissue injury.

The present invention therefore relates to a method for the prevention and/or treatment of a retinal degenerative diseases and/or a tissue injury, which comprises administering to a subject in need thereof a medicament or a composition described above, which comprises a synthetic peptide consisting of the amino acid sequence set forth as $X_1X_2X_3X_4EX_5$ (SEQ ID NO: 1), wherein, $X_1$ is serine (S), or alanine (A);
$X_2$ is leucine (L), alanine (A) or isoleucine (I);
$X_3$ is glycine (G), alanine (A), valine (V) or asparagine (N);
$X_4$ is alanine (A), glycine (G) or glutamic acid (E);
$X_5$ is glutamine (Q), alanine (A) or asparagine (N); and
$X_2, X_3, X_4,$ and $X_5$ are independently in L-form, while $X_1$ and E are independently in L- or D-form; and in the case when the SEQ ID NO: 1 has the sequence of SLGAEQ (SEQ ID NO: 9), then the serine (S) or the glutamic acid (E) is in D-form; and a pharmaceutically acceptable carrier.

Alternatively or optionally, the N-terminus of the amino acid sequence of the synthetic peptide is acetylated and the C-terminus of the amino acid sequence is amidated.

The medicament and/or composition when administrated to the subject is capable of ameliorating or alleviating the symptoms associated with the retinal degenerative disease and/or the condition in need of tissue repair or regeneration.

In particular embodiments, the synthetic peptide is selected from the group of peptides described above, which include and are not limited to, 6-mer Sa, 6-mer La, 6-mer Ga, 6-mer Ag, 6-mer Qa, 6-mer Li, 6-mer Gv, 6-mer Gn, 6-mer Ae, 6-mer Qn, 6-mer dS, 6-mer dE, and a combination thereof.

According to one embodiment, the present invention is related to a method for treating retinal degenerative disease, particularly, diabetic retinopathy, age-related macular degeneration (AMD), retinitis pigmentosa (RP), glaucoma, or acute UV retinopathy, which comprises administering to a subject in need thereof a medicament or a composition of the present invention.

According to another embodiment, the present invention is related to a method for treating a tissue injury that requires tissue repair or regeneration, particularly, dry eye disease (DED), osteoarthritis, acute tendon rupture, skin wound, skin aging, wrinkle, alopecia, or retinal ischemia/reperfusion (I/R) injury, which comprises administering to a subject in need thereof a medicament or a composition of the present invention.

The method includes the step of, administering to a subject in need thereof a medicament or a composition of the present invention.

In all embodiments, the subject suitable for treatment is a human

The present invention will now be described more specifically with reference to the following embodiments, which are provided for the purpose of demonstration rather than limitation.

EXAMPLES

Materials and Methods

Materials

Dulbecco's modified Eagle's medium (DMEM) and fetal bovine serum (FBS) were purchased from Invitrogen (Carlsbad, CA). Phospho-Stat3 (Tyr705) and STAT3 antibody were purchased from Cell Signaling Technology (Danvers, MA). STAT3 peptide inhibitor (no. 573096) and STAT3 Inhibitor V (no. 573099) were purchased from Calbiochem (La Jolla, CA). Glutamate, dimethyl sulfoxide (DMSO), streptozotocin (STZ; S0130), fluorescein isothiocyanate-bovine serum albumin (FITC-BSA), and all chemicals were all from Sigma-Aldrich (St. Louis, MO). Short synthetic peptides were synthesized by GenScript (Piscataway, NJ), and each peptides were modified by acetylation at the NH2-termini and amidation at the COOH-termini for stability, and characterized by mass spectrometry (>95% purity).

Cell Culture

The C2C12 mouse myoblast cell line and Neuro-2a mouse neuroblast cell line were from the American Type Culture Collection (ATCC, Manassas, VA). Cells were maintained in DMEM-high-glucose medium. ARPE-19 cells, a human retinal pigment epithelial cell line, were cultured in DMEM/F12 (1:1 mixture of Dulbecco's modified Eagle's medium and Ham's F12). All media were supplemented with 10% FBS, 4 mM 1-glutamine, 1 mM pyruvate, and 100 U/ml penicillin-100 µg/ml streptomycin at 37° C. in the presence of 5% $CO_2$ atmosphere.

Assessment of Neuro-2a Cell Death

Neuro-2a cells were seeded in 48-well culture plates $(1.5\times10^5$ cells/well) for 24 h, and then cultured in 0.5 ml fresh 2% FBS-DMEM medium containing 20 µM of the present peptide (7 µg of 6-mer in 0.5 ml medium) for further 4 h. Subsequently, 100 mM glutamate (from 1 M stock and PBS as solvent) was added to cells for further 6 h. Glutamate-induced cell death was quantitatively assessed by measuring lactate dehydrogenase (LDH) activity released into the culture medium by damaged cells. LDH activity was measured using PicoProbe™ LDH-Cytotoxicity Fluorometric Assay Kit (Catalog #K314-500; BioVision) according to the instruction manuals. LDH activity was estimated using an automated microplate reader (UVmax; Molecular Devices, San Francisco, CA) by measuring the fluorescent product (Ex/Em=535/587 nm).

Western Blot Analysis

Cell lysis, fractionation, and SDS-PAGE were conducted in accordance with procedures described previously (Yang Y C et al., BMC Cancer 2007; 7:216). Antibodies used in this study were for Phospho-Stat3 and STAT3 (1:1000-fold dilution). Proteins of interest were detected using the appropriate IgG-HRP secondary antibody (Santa Cruz Biotechnology) and ECL reagent (Amersham Biosciences).

Quantitative Real-Time PCR

Total RNA was extracted from cells using TRIzol (Invitrogen). Synthesis of cDNA was performed with 1 µg of total RNA at 50° C. for 50 min using oligo(dT) primers and reverse transcriptase (Superscript III; Invitrogen). Briefly, quantification of cDNA was performed in the LightCycler (Roche, Mannheim, Germany) using the DNA Master SYBR Green I kit (Roche) with the following cycling conditions: initial denaturation at 95° C. for 10 min, followed by 40 cycles at 95° C. for 10 s, 60° C. for 10 s, and 72° C. for 10 s and a 5-min terminal incubation at 72° C. The data were calculated with ΔΔCt. The expression was then normalized against the expression of glyceraldehyde-3-phosphate dehydrogenase (GAPDH). The PCR primers were mouse Survivin sense, 5'-TGCCACGATGGTGAT-GAAAC-3' (SEQ ID NO: 27), anti-sense, 5'-TGACGGGTAGTCTTTGCAGT-3' (SEQ ID NO: 28) (accession number: NM_001012273.1; PCR product: 136 bp); mouse GAPDH sense, 5'-AACGGATTTGGCCGTAT-TGG-3' (SEQ ID NO: 29), anti-sense, 5'-CAT-TCTCGGCCTTGACTGTG-3' (SEQ ID NO: 30) (NM_001289726.1; 149 bp). For analysis rabbit inflammatory gene expression, The PCR primers were rabbit TNF-αsense, 5'-CCTGTGCCTCCCTTCACTTA-3' (SEQ ID NO: 31), anti-sense, 5'-CCCTTAGGGAGCAGAGGTTC-3' (SEQ ID NO: 32) (accession number: NM 001082263.1); rabbit IL-1βsense, 5'-CCTGTTCTTTGAGGCCGATG-3' (SEQ ID NO: 33), anti-sense, 5'-GCCG-GAAGCTCTTGTTGTAG-3' (SEQ ID NO: 34) (NM 001082201.1); rabbit GAPDH sense, 5'-AGGTCATC-CACGACCACTTC-3' (SEQ ID NO: 35), anti-sense, 5'-GT-GAGTTTCCCGTTCAGCTC-3' (SEQ ID NO: 36) (accession number:NM 001082253.1). The cycle threshold (Ct) values of the PCR product and a GAPDH (Glyceraldehyde 3-phosphate dehydrogenase) control mRNA were used to calculate relative quantities of mRNA.

Animal Studies

All experiments were approved by the Mackay Memorial Hospital Review Board (Taiwan). Animal investigation and ophthalmic surgeries were conducted according to the Association for Research in Vision and Ophthalmology Statement for the Use of Animals in Ophthalmic and Vision Research. All surgeries were performed under aseptic conditions.

RetinalIschemia-Reperfusion (I/R) Animal Model

Experimental procedures were approved by the Mackay Memorial Hospital Review Board (Taiwan, R.O.C.). All surgeries were performed under aseptic conditions. Adult 10-week-old male Sprague-Dawley rats (initial body weight=312±11 g) were anesthetized by an intraperitoneal injection of xylazine (10 mg/kg). Peptide was dissolved in 0.85% normal saline to 1 mM and delivered by the subconjunctival injection of 100 µL peptide through a 31-Gneedle with a micro-syringe before the induction of I/R. Normal saline was as a vehicle control. Rat I/R was performed after peptide or vehicle injection for 4 h. Pupils were dilated with 0.5% tropicamide and 0.5% phenylephrine. Body temperature was maintained at 37° C. using a heating blanket After dilation of the pupil, the anterior chamber of the right eye was cannulated with a 27-gauge needle connected to a physiological saline reservoir. The intraocular pressure (IOP) was raised to 110 mmHg by keeping the reservoir at 150 cm above the eye, and retinal ischemia was confirmed by observing whitening of the iris and the loss of the red reflex of the retina. After 90 min of ischemia, the cannulating needle was withdrawn and the IOP was returned to normal pressure, resulting in recovery of the blood supply from the retinal artery and reperfusion injury induced. The reperfusion was evident by the return of the red reflex. Corneal analgesia was achieved using 1 or 2 drops of 0.4% oxybuprocaine hydrochloride, and Ofloxacin ophthalmic gel (0.3%) was applied topically to the eye before and after the procedure. Only the right eye was used in all experiments. A sham procedure was performed at left eye served as an intra-animal control.

Histological Evaluation of UR-induced Retinal Injury

Rats (n=6 in each group) were euthanized using an overdose of pentobarbital (intravenously 100 mg/kg of bodyweight) at 14 days after the I/R injury, the eyeballs were marked at the 12 o'clock position of the cornea with silk suture, and then enucleated and fixed in 4% paraformaldehyde(PFA) at 4° C. for 24 h. After fixation, the anterior segment was removed, and the posterior eyeball containing the optic disc was dehydrated in a graded ethanol series and embedded in paraffin. For hematoxylin and eosin (H&E) staining, 5 µm thick sections were taken along the vertical meridian through the optic nerve head using a microtome and observed under a light microscope (Leica, Heidelberg, Germany) equipped with a CCD camera at 200×. To quantify the degree of I/R damage in the retina, we measured the overall central retinal thicknesses (OT, between the GCL to ONL), the inner nuclear layer (INL), and the outer nuclear layer (ONL). The number of cells in the ganglion cell layer (GCL) was calculated using the linear cell density (cells per 200 µm). Three sections per eye were averaged and the mean of six eyes was recorded as the representative value for each group.

TUNEL Staining of UR-Injured Retina

After I/R for 20 h, rats (n=6 in each group) were euthanized by an overdose of pentobarbital. Enucleated eyeballs were fixed in 4% PFA for 24 h at 4° C. Fixed retinal tissues were embedded in paraffin. To identify apoptosis of retinal cells, 5 µm sections thick cut through the optic disc, deparaffinized, rehydrated, incubatedwith 20 µg/mL proteinase K for 10 min, and immunofluorescence staining of apoptotic cells was performed using a terminal deoxynucleotidyl transferase(TdT)-mediated dUTP nick-end labeling (TUNEL)-based kit (Roche Molecular Biochemicals, Indianapolis, IN) according to the manufacturer's instructions. Nuclei were located by counterstaining with Hoechst 33258 for 7 min Sections were observed under an epifluorescence microscope (Zeiss Axioplan 2 imaging; Zeiss, Oberkochen, Germany) equipped with a charge-coupled device (CCD) camera (Zeiss AxioCam HRm, Zeiss) (×400, 6 fields/sample), and quantification was performed using Axiovert software (Zeiss AxioVision Release 4.8.2, Zeiss). Three sections per eye were averaged and the mean of six eyes was recorded as the representative value for each group.

Immunofluorescence Staining

Deparaffinized retinal sections were blocked with 10% goat serum and 5% bovine serum albumin (BSA) in PBS containing 0.5% TritonX-100 (PBST) for 20 min at room temperature for blocking nonspecific staining. Staining was performed using primary antibodies against glial fibrillary acidic protein (GFAP) (1:100 dilution) or Iba-1 (1:100 dilution) at 37° C. for 3 h. The slides were subsequently incubated with the appropriate fluorescent-labeled secondary antibodies (1:500 dilution) at 37° C. for 1 h and then counterstained with Hoechst 33258 for 6 min. The slides were then rinsed with PBST three times, mounted with FluorSave™ reagent (Calbiochem) and viewed with an epifluorescence microscope (Zeiss Axioplan 2 imaging; Zeiss, Oberkochen, Germany) Three sections per eye were averaged and the mean of six eyes was recorded as the representative value for each group.

Preparation and Analysis of Retinal Vasculature

Rats (n=6 in each group) were euthanized using an overdose of pentobarbital at 14 days after I/R injury, the eyeballs were fixed with 4% PFA for overnight at 4° C. Retinas were isolated, permeabilized with PBST for 5 min, washed in water overnight, placed on glass slide and incubated with 2.5% trypsin (50 µl, Invitrogen, Carlsbad, CA) at 37° C. for 30 min and occasionally shaken gently. Nonvascular cells were gently brushed away from the vasculature, and washed by PBS. Sections were then stained with iso-lectin GS-IB4 (Alexa Fluor 568 conjugate, 1:200 dilution, Thermo Fisher Scientific) at 37° C. for 1 h and then counterstained with Hoechst 33258 for 10 min, rinsed with PBST, then mounted with FluorSave™ reagent and visualized under an epifluorescence microscope at 200×. Degenerate capillaries were identified as small vessel tubes with no pericytes anywhere along their lengths and are reported per square millimeter of retinal area. Ten sections per eye were averaged and the mean of six eyes was recorded as the representative value for each group.

Measurement of Vascular Abnormalities in the Retina of Diabetic Mice

Diabetic mice were generated by intraperitoneal injection of streptozotocin (STZ; 200 mg/kg body weight) at day 1 and day 3. STZ was freshly prepared in 0.1 M citrate buffer (pH 4.5). After injection, mice were supplied with 10% sucrose overnight to prevent sudden hypoglycaemic shock. After 1 week (day 7), mice with non-fasting blood glucose levels >500 mg/dl were defined as diabetic and used for the experiments. Balanced salt solution (BSS) was served as peptide vehicle (Alcon, Novartis). 6-mer analogues (dissolved in BSS to 200 µM) eye drop were topically administered to eyes three times a day. After 2 weeks (day 14), mice were intraperitoneal injection of 100 mg/kg of FITC-BSA for further 30 min to determine vascular lesions (hemorrhaging areas) in retina. Subsequently, the animals were euthanized by $CO_2$ inhalation, and the eyes were enucleated and fixed with 4% PFA for overnight at 4° C and flat-mounted onto glass slides to obtain optical sections. Vascular lesions in the retina was scored in all four retinal quadrants of flat mounts by an epifluorescence microscopy at 200×. Three microscopic fields were sampled in each quadrant in both the central and peripheral retina, and data were presented as the average number of lesions/retina.

Dry Eye Animal Model

Animals

C57BL/6 mice (7-8 weeks old, each weighted about 18 to 25 g) were used in this model system. All mice were maintained in the animal facility in accordance with the procedures approved by Mackay Memorial Hospital Review Board (Taiwan, R.O.C.). All animal experimental procedures were conducted according to the ARVO Statement for the Use of Animals in Ophthalmic and Vision Research.

Dry Eye Induction

Dry eyes were induced by placing mice in a controlled environment chamber (CEC) for 14 days in accordance with procedures previously described by Barabino et al (IVOS (2005) 46(8), 2766-2771). Mice placed in the CEC were exposed to a condition, in which relative humidity (RH) was maintained at <25%, temperature at 20-22° C., and airflow at about 15 L/min, for 12 hours per day. Control mice were kept in a normal environment (RH>50%, no air flow, temperature of 20-22° C.) for the same duration.

Treatment

A common artificial tear formulation, 1% carboxymethylcelllulose (CMC) dissolved in balanced salt solution (BSS) was used as the peptide vehicle. Peptide (100 μM, about 0.7 μg peptide in 10 μl eye drop used for treating one eye) or 1% CMC vehicle was topically administered to eyes three times a day. To test whether the present synthetic peptide could exert any therapeutic action on dry eyes, mice were housed at CEC for 14 days without topical treatment, and then were treated with the present peptide for 4 days.

Corneal Fluorescein Staining

Animals were anesthetized by an intraperitoneal injection of a mixture of zoletil (6 mg/kg) and xylazine (3 mg/kg). Corneal epithelial injury was determined by staining with topical fluorescein (Fluor-I-Strip, Ayerst Laboratories, Philadelphia, PA). Corneal fluorescein staining was examined with a slit-lamp biomicroscope under cobalt blue light and photographed with a digital camera. Dye staining of the cornea was scored in a blinded manner as follows: score 0 for no punctuate staining; score 1 when less than one third of the cornea was stained; score 2 when two thirds or less was stained; and score 3 when more than two thirds was stained (Horwath-Winter J 2013).

Corneal Epithelial Cell Culture and Treatment

Limbal stem epithelial cells (LSEC) were isolated from 6-month-old New Zealand white rabbits and continuously cultivated for 14 days byDMEM/F-12basalmedium based cell-suspension culture to achieve corneal-liked epithelial cell differentiation as previously described (Ho et al., Stem Cells. 2013; 31:1775). LSEC ($2 \times 10^5$ cells per well of 6-well plate) were treated with 2% FBS-containing basal medium mixed with 20 μM 6-mer variant peptide for 6 h and then directly treated with 90 mM NaCl, leading cells suffered hyperosmotic pressure (HOP). After 3 h, quantitative real-time PCR was used to estimate HOP-induced Tumor necrosis factor (TNF)-α and nterleukin-1 beta (IL-1β) expressions. Cells cultured in DMEM/F-12basalmedium (309 mOsm) was used as negative control.

Statistics

Results were generated in three independent experiments. All numerical values were expressed as the mean±SD. Comparisons of two groups were done using the Mann-Whitney test. $P<0.05$ was considered significant.

Example 1 Identification and Characterization of Neuroprotective Peptides 1.1 Identifying Neuroprotective Peptide In this example, a series of short synthetic peptides as listed in Table 2 were synthesized, and their neuroprotective effects were evaluated by glutamate-induced cell death in Neuor-2a neuroblast cells in accordance with procedures described in "Material and Methods" section. In addition, the first amino acid residue (i.e., serine) of each synthetic peptide (SEQ ID NOs: 2-11) was in D-form so to increase protease resistance.

Figure 1:
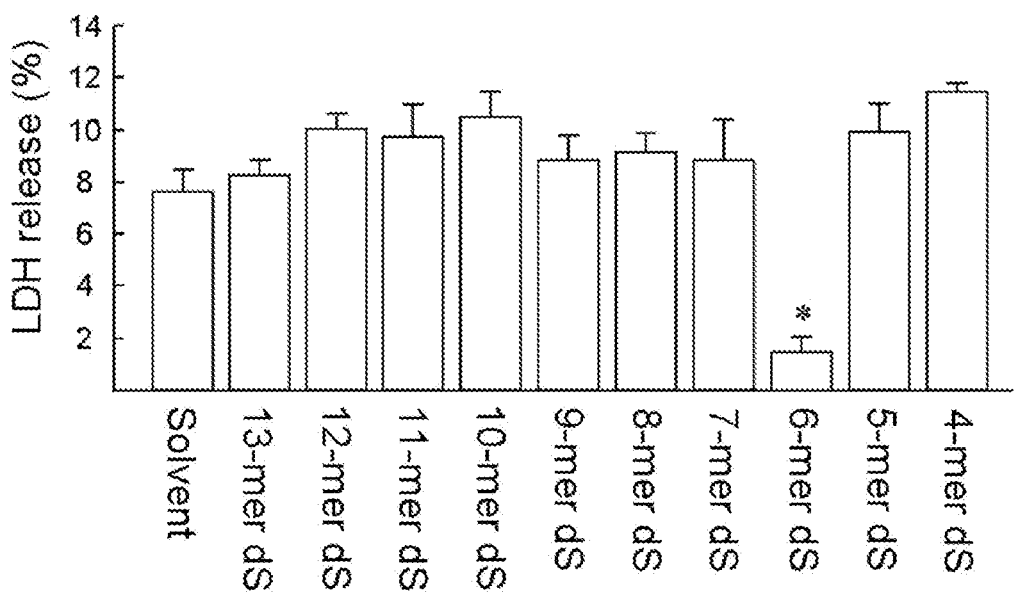
FIG. 1. Analysis of the effect of the present short synthetic peptides on glutamate-induced Neuro-2a cell death. Cells were pretreated with the synthetic peptides for 4 h. Measurements of LDH release into the medium of Neuro-2a cells after 6-hour exposure to the 100 mM glutamate, expressed as mean±SD (n=6). *P<0.05 versus solvent/glutamate-treated cells.

Briefly, cells were pretreated with the designated peptide (i.e., any of SEQ ID NOs: 2 to 11) for 4 h and then treated with 100 mM glutamate for 6 h. The cell death was detected by a commercial lactate dehydrogenase (LDH) Cytotoxicity Assay Kit. Results are depicted in FIG. 1.

TABLE 2

Short synthetic peptides with

| Peptide Name | Amino Acid Sequence | SEQ ID NO |
|---|---|---|
| 13-mer-dS | $NH_2$-(D-Ser)-Leu-Gly-Ala-Glu-Gln-Arg-Thr-Glu-Ser-Ile-Ile-His-COOH<br>SLGAEQRTESIIH | 2 |
| 12-mer-dS | $NH_2$-(D-Ser)-Leu-Gly-Ala-Glu-Gln-Arg-Thr-Glu-Ser-Ile-Ile-COOH<br>SLGAEQRTESII | 3 |
| 11-mer-dS | $NH_2$-(D-Ser)-Leu-Gly-Ala-Glu-Gln-Arg-Thr-Glu-Ser-Ile-COOH<br>SLGAEQRTESI | 4 |
| 10-mer-dS | $NH_2$-(D-Ser)-Leu-Gly-Ala-Glu-Gln-Arg-Thr-Glu-Ser-COOH<br>SLGAEQRTES | 5 |
| 9-mer-dS | $NH_2$-(D-Ser)-Leu-Gly-Ala-Glu-Gln-Arg-Thr-Glu-COOH<br>SLGAEQRTE | 6 |
| 8-mer-dS | $NH_2$-(D-Ser)-Leu-Gly-Ala-Glu-Gln-Arg-Thr-COOH<br>SLGAEQRT | 7 |

TABLE 2-continued

Short synthetic peptides with

| Peptide Name | Amino Acid Sequence | SEQ ID NO |
|---|---|---|
| 7-mer-dS | NH$_2$-(D-Ser)-Leu-Gly-Ala-Glu-Gln-Arg-COOH<br>SLGAEQR | 8 |
| 6-mer-dS | NH$_2$-(D-Ser)-Leu-Gly-Ala-Glu-Gln-COOH<br>SLGAEQ | 9 |
| 5-mer-dS | NH$_2$-(D-Ser)-Leu-Gly-Ala-Glu-COOH<br>SLGAE | 10 |
| 4-mer-dS | NH$_2$-(D-Ser)-Leu-Gly-Ala-COOH<br>SLGA | 11 |

The bold letter in any sequence indicates that particular amino acid is in D-form.

As depicted in FIG. 1, glutamate led to cell death over time (7.6±0.8%; peptide solvent DMSO added with glutamate was used as a positive control). Interestingly, it was found that only the 6-mer-dS peptide (SLGAEQ; SEQ ID NO: 9) exhibited protective effect on Neuro-2a cells, whereas neither the peptides having more than 6 amino acid residues (i.e., 13-mer dS to 7-mer dS (SEQ ID NOs: 2 to 8) nor the peptides having less than 6 amino acid residues (i.e., 5-mer dS or 4-mer dS (SEQ ID NOs: 10 or 11) exhibited any cell protective effect (1.5±0.5% versus 8.2±0.6%–11.4±0.3%).

The results implied that the sixth amino acid residue (Gln; Q) in the 6-mer dS (SLGAEQ; SEQ ID NO: 9) is a critical residue that preserves the neuroprotective activity of the 6-mer. The results also suggest that arginine (R) residue (the last amino acid of 7-mer dS (SEQ ID NO: 8) may play an inhibitory role on the bio-function of the 6-mer.

1.2 Characterization of the 6-mer dS Peptide

1.2.1 6-mer dS Peptide Induces Survivin Expression via STAT3 Dependent Manner Survivin is a transcriptional target of STAT3 (signal transducer and activator of transcription) critical to neural cell survival during ischemia. Accordingly, whether STAT3 signaling plays a role on the neuroprotective effect of the 6-mer dS was investigated in this example. Results are illustrated in FIG. 2.

Western blot analysis revealed that C2C12 myoblast cells stimulated by 6-mer dS led to STAT3 phosphorylation, which occurred in a period of 5 to 20 min after the stimulation. By contrast, the 5-mer dS possessed no such effect (FIG. 2, panel A).

Figure 2:
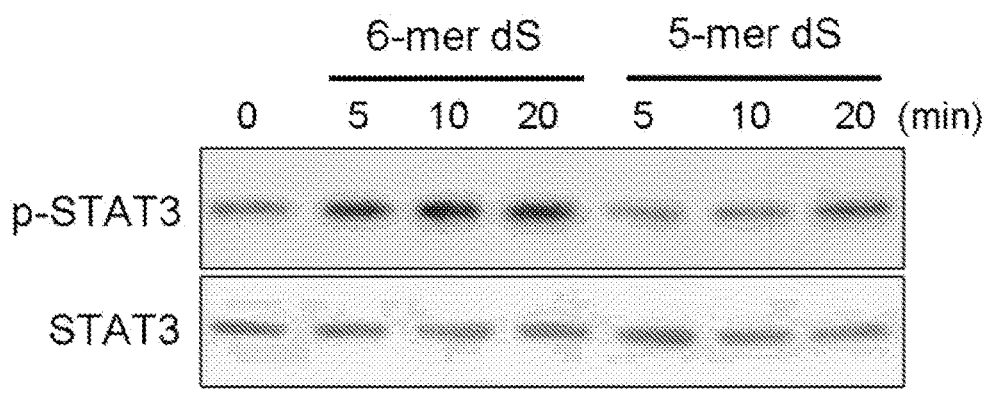
FIG. 2. The 6-mer dS induced survivin expression in C2C12 cells was via STAT3 dependent manner. (A) Representative immunoblots showed the effect of 6-mer dS or 5-mer dS on phosphorylation of STAT3. The STAT3 was used as a loading control. (B) Real-time qPCR analysis of the expression of survivin gene induced by the synthetic peptides of various lengths or STAT3 inhibitors. *P<0.002 versus solvent-treated cells.
Figure 2:
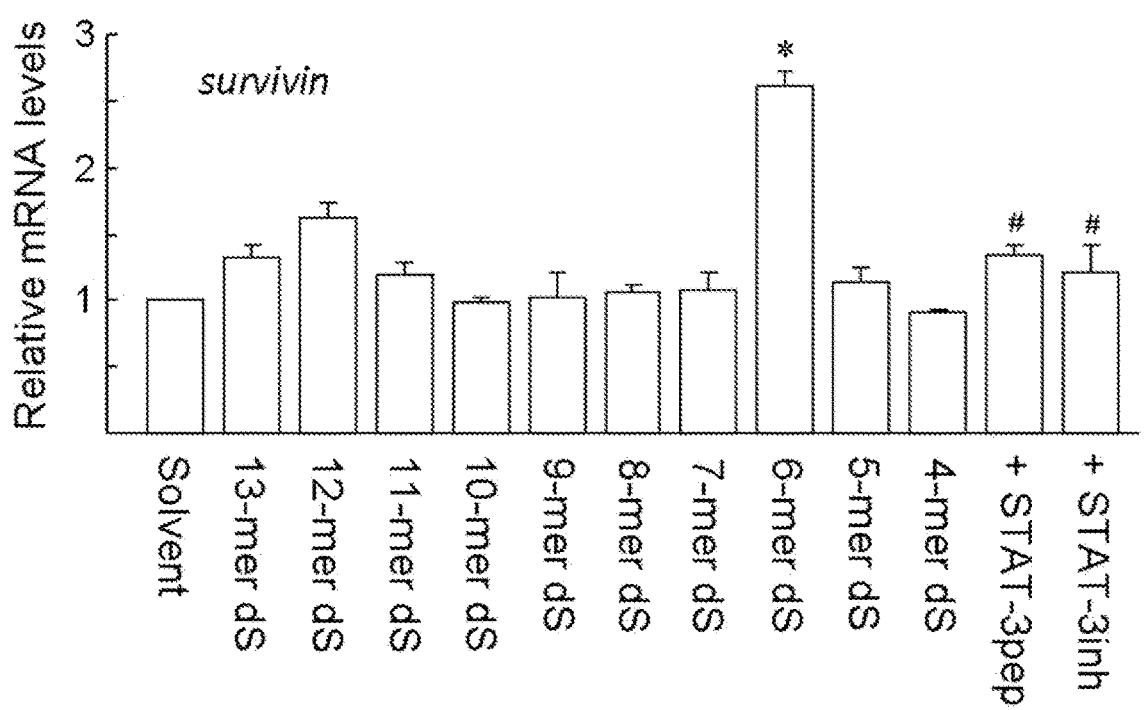

Further, after being stimulated with the 6-mer dS for 3 h, the level of survivin mRNA in C2C12 cells significantly increased by 2.6-fold, as compared to that of the solvent-treated cells (FIG. 2, panel B). C2C12 cells treated with other peptides (i.e., any of SEQ ID NOs: 2-8 or 10-11) resulted in no such induction.

Known pharmacological inhibitors, including STAT3pep and STAT3 inhibitor V, were also used to explore the molecular mechanism of the survivin induction. The real-time qPCR assay revealed that survivin mRNA expression induced by the 6-mer dS was suppressed in cells pretreated with STAT3 inhibitors (i.e., STAT3pep or STAT3 inhibitor V), from 2.6-fold to 1.3-fold. (FIG. 2, panel B)

Taken together, the findings in this example suggested that the 6-mer dS peptide exerted its neuroprotective effect by inducing survivin expression through the activation of the STAT3 signaling pathway.

1.2.2 Glutamic Acid Residue is Critical for Survivin Expression Induced by the 6-mer dS Peptide To further investigate the critical residues in the 6-mer dS peptide, alanine scanning and amino acid substitution were respectively used to create 6-mer variants, in which residues in the 6-mer dS peptide were systematically substituted by alanine, or by its D-form amino acid, or were mutated; the thus created 6-mer variants are listed in Tables 3 to 4.

TABLE 3

The 6-mer variants created by alanine scanning approach

| Peptide Name | Amino Acid Sequence | SEQ ID NO |
|---|---|---|
| 6-mer Sa | NH$_2$-Ala-Leu-Gly-Ala-Glu-Gln-COOH<br>ALGAEQ | 12 |
| 6-mer La | NH$_2$-Ser-Ala-Gly-Ala-Glu-Gln-COOH<br>SAGAEQ | 13 |
| 6-mer Ga | NH$_2$-Ser-Leu-Ala-Ala-Glu-Gln-COOH<br>SLAAEQ | 14 |
| 6-mer Ag | NH$_2$-Ser-Leu-Gly-Gly-Glu-Gln-COOH<br>SLGGEQ | 15 |
| 6-mer Ea | NH$_2$-Ser-Leu-Gly-Ala-Ala-Gln-COOH<br>SLGAAQ | 16 |
| 6-mer Qa | NH$_2$-Ser-Leu-Gly-Ala-Glu-Ala-COOH<br>SLGAEA | 17 |

TABLE 4

The 6-mer variants created by substitution with D-form amino acid

| Peptide Name | Amino Acid Sequence | SEQ ID NO |
|---|---|---|
| 6-mer dS | NH$_2$-(D-Ser)-Leu-Gly-Ala-Glu-Gln-COOH<br>SLGAEQ | 9 |
| 6-mer dL | NH$_2$-Ser-(D-Leu)-Gly-Ala-Glu-Gln-COOH<br>SLGAEQ | 9 |
| 6-mer dA | NH$_2$-Ser-Leu-Gly-(D-Ala)-Glu-Gln-COOH<br>SLGAEQ | 9 |
| 6-mer dE | NH$_2$-Ser-Leu-Gly-Ala-(D-Glu)-Gln-COOH<br>SLGAEQ | 9 |
| 6-mer dQ | NH$_2$-Ser-Leu-Gly-Ala-Glu-(D-Gln)-COOH<br>SLGAEQ | 9 |

The bold letter in any sequence indicates that particular amino acid is in D-form.

TABLE 5

The 6-mer variants created by mutation

| Peptide Name | Amino Acid Sequence | SEQ ID NO |
|---|---|---|
| 6-mer St | NH$_2$-The-Leu-Gly-Ala-Glu-Gln-COOH<br>TLGAEQ | 18 |
| 6-mer Li | NH$_2$-Ser-Ile-Gly-Ala-Glu-Gln-COOH<br>SIGAEQ | 19 |
| 6-mer Gv | NH$_2$-Ser-Leu-Val-Ala-Glu-Gln-COOH<br>SLVAEQ | 20 |
| 6-mer Gn | NH$_2$-Ser-Leu-Asn-Ala-Glu-Gln-COOH<br>SLNAEQ | 21 |
| 6-mer Ae | NH$_2$-Ser-Leu-Gly-Glu-Glu-Gln-COOH<br>SLGEEQ | 22 |
| 6-mer Ai | NH$_2$-Ser-Leu-Gly-Ile-Glu-Gln-COOH<br>SLGIEQ | 23 |
| 6-mer As | NH$_2$-Ser-Leu-Gly-Ser-Glu-Gln-COOH<br>SLGSEQ | 24 |
| 6-mer Ed | NH$_2$-Ser-Leu-Gly-Ala-Asp-Gln-COOH<br>SLGADQ | 25 |
| 6-mer Qn | NH$_2$-Ser-Leu-Gly-Ala-Glu-Asn-COOH<br>SLGAEN | 26 |

Figure 3:
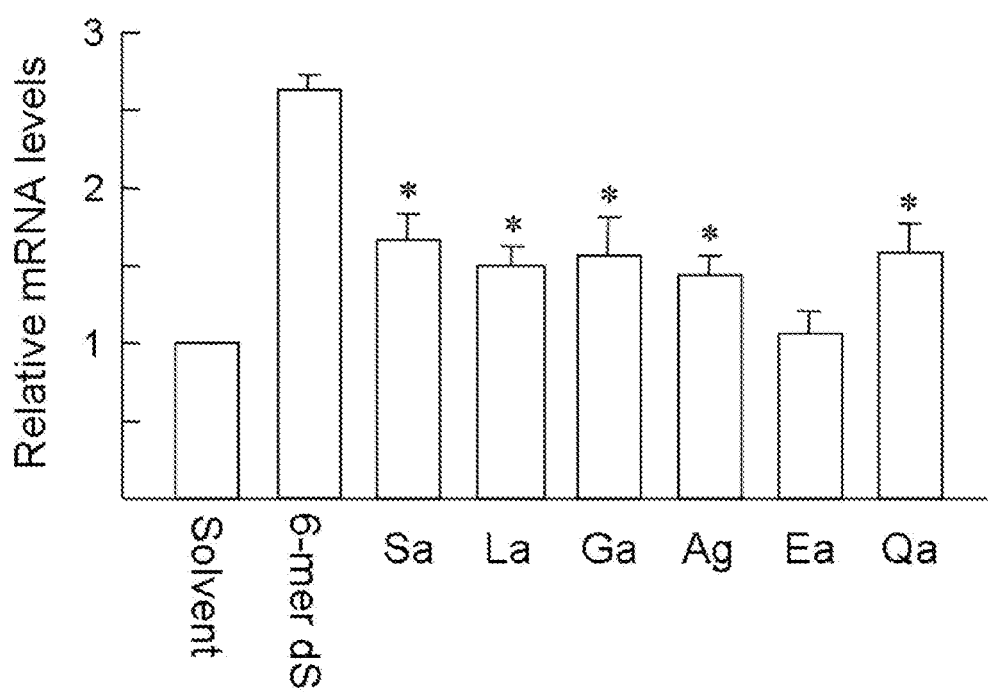
FIG. 3. Effect of 6-mer variant created by alanine scanning approach on the survivin mRNA induction in C2C12 cell. Three independent assays were performed, and data are represented as the mean±S.D. *P<0.04 versus solvent control.

Similar to the approach in Example 1.2.1, the expression level of survivin mRNA in C2C12 cells was used as an indicator for the function of the 6-mer variants in Tables 3 to 5. Briefly, C2C12 cells in low serum media were treated with 20 µM the 6-mer variants for 6 h. Real-time qPCR assay revealed that 6-mer Sa (1.7-fold), 6-mer La (1.5-fold), 6-mer Ga (1.6-fold), 6-mer Ag (1.5-fold) and 6-mer Qa (1.6-fold) were capable of partially retaining the 6-mer dS activity in terms of the survivin induction (*$P<0.004$ versus solvent control; FIG. 3). The results also confirmed that alanine substation at the glutamic acid (E) residues would severely impair the 6-mer activity.

Figure 4:
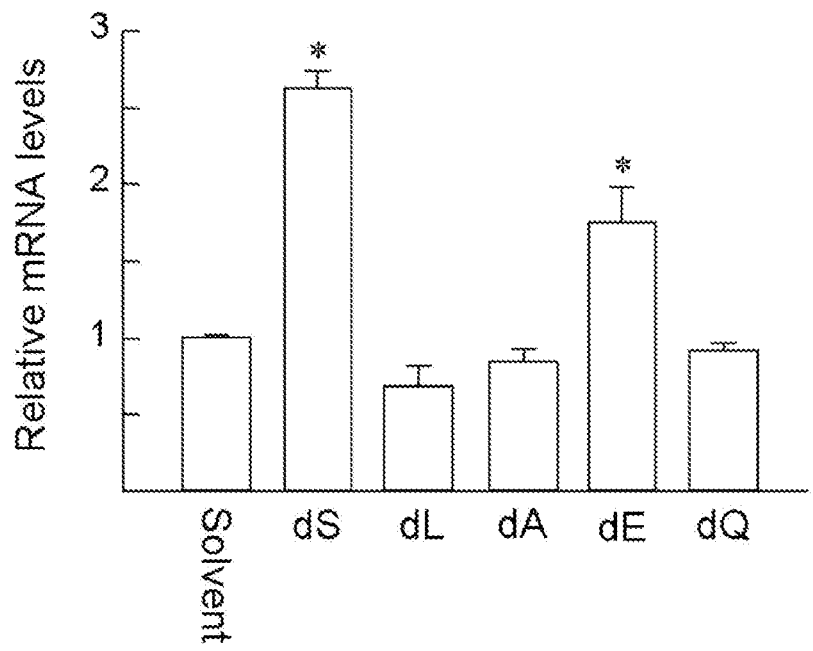
FIG. 4. The effect of 6-mer variants created by substitution with D-form amino acids on the survivin mRNA induction in C2C12 cell. Three independent assays were performed, and data are represented as the mean±S.D. *P<0.05 versus solvent control.

As to the function of 6-mer variants created by substitution with its non-natural amino acids (D-form amino acids), real-time qPCR assay revealed that substitution of serine (S) with its D-form residue increased the level of survivin mRNA, as compared to that of the solvent control (FIG. 4, dS vs solvent), thus 6-mer dS served as a positive control, whereas substitution of leucine (L), alanine (A) or glutamine (Q) with its corresponding D-form residue would hamper the survivin gene induction activity significantly (FIG. 4, dL, dA or dQ vs 6-mer dS). Substitution of glutamic acid (E) with its D-form residue resulted in a moderate induction on survivin mRNA level (FIG. 4, dE vs 6-mer dS), which the level was still significantly higher than that of the solvent control.

Figure 5:
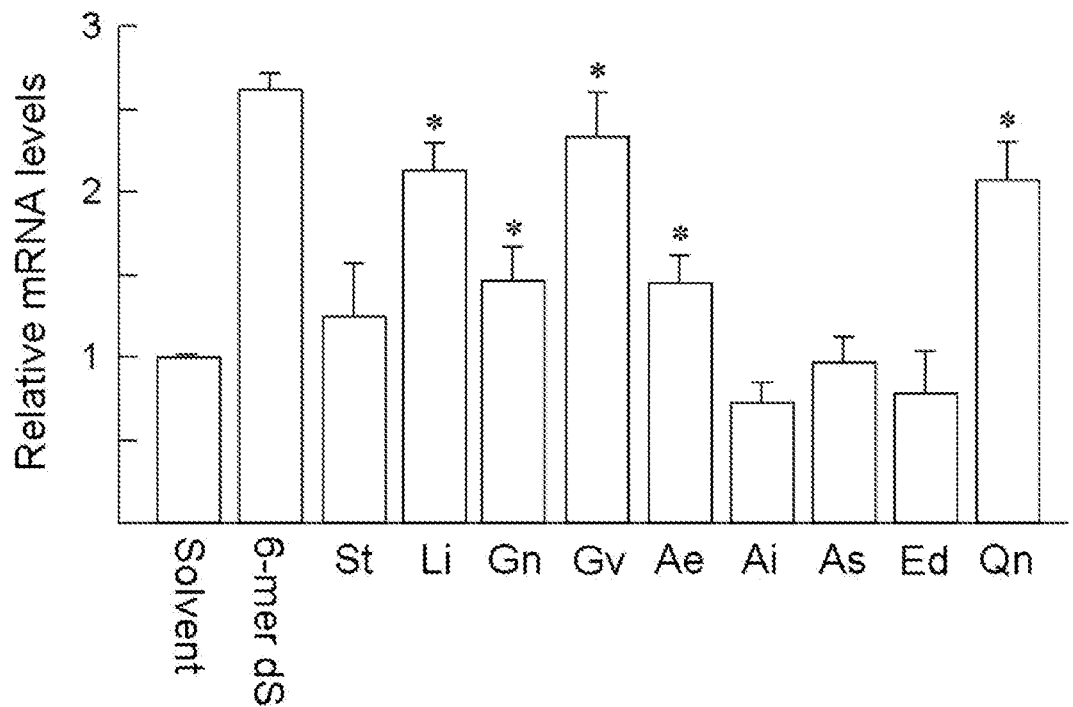
FIG. 5. The effect of 6-mer variants created by amino acid substitution on the survivin mRNA induction in C2C12 cell. Three independent assays were performed, and data are represented as the mean±S.D. *P<0.05 versus solvent control.

As amino acids are usually classified by the property of the side chain (i.e., R group), thus mutations were created by replacing the amino acid residues in the 6-mer with other residues that exhibited similar property in the R group (see Table 5). Real-time qPCR assay in FIG. 5 revealed that the replacing leucine (L) with isoleucine (I) (6-mer Li), glycine (G) with asparagine (N) (6-mer Gn), glycine (G) with valine (V) (6-mer Gv), alanine (A) with glutamic acid (E)(6-mer Ae), or glutamine (Q) with asparagine (N) (6-mer Qn) could independently induce survivin mRNA by 2.1-, 1.5-, 2.3-, 1.5- and 2.1-folds, as compared to that of the solvent control (FIG. 5; *$P<0.05$). By contrast, replacing serine (S) with threonine (T) (6-mer St), alanine (A) with isoleucine (I) (6-mer Ai), alanine (A) with serine (6-mer As), or glutamic acid (E) with aspartic acid (D) (6-mer Ed) severely impaired the survivin mRNA induction (i.e., same or below the basal level).

Collectively, the results suggested that 5 out of the 6 residues of the 6-mer dS (SEQ ID NO: 9) may tolerate amino acid substitution, while the glutamic acid residue (E) is critical for the neuroprotective activity of the 6-mer peptide.

Example 2 6-mer dS, 6-mer Sa, 6-mer Li, 6-mer Gv, and 6-mer Qn Protects Retina Against Retinal Ischemia/Reperfusion Injury Many ocular diseases, such as retinal vascular occlusion, acute glaucoma, diabetic retinopathy, age-related macular degeneration (AMD), retinal detachment and retinopathy of prematurity are associated with retinal ischemia/reperfusion (I/R) injury, which may lead to blindness in these patients. Usually retinal ischemia is due to capillary blockage, resulting in energy depletion in a region of retina, subsequent natural reperfusion would induce strong oxidative stress. A few hours after I/R injury, inflammation and cell death occurs. Eventually, these pathological response would lead to optic nerve and retinal capillary degenerations.

In this example, the neuroprotective effect of the 6-mer variant peptides on neural retina cells and retinal capillary system was investigated using a rat model of I/R injury described in the "Material and Methods" section. Briefly, 6-mer variant peptide (1 mM, 120 µl) was injected into the subconjunctival space of Sprague-Dawley rats for 4 h before the induction of I/R. Then, I/R injury was induced in rat retinas by increasing the intraocular pressure (IOP) in the eye to 110 mmHg for 90 min, followed by 20 h of reperfusion. Subsequently, the level of retinal cell apoptosis was evaluated using TUNEL staining. In addition, the retinal morphology was analyzed with H&E staining 14 days after the I/R injury. Results are summarized in FIGS. 6 to 10, and Tables 6 to 9.

Figure 6:
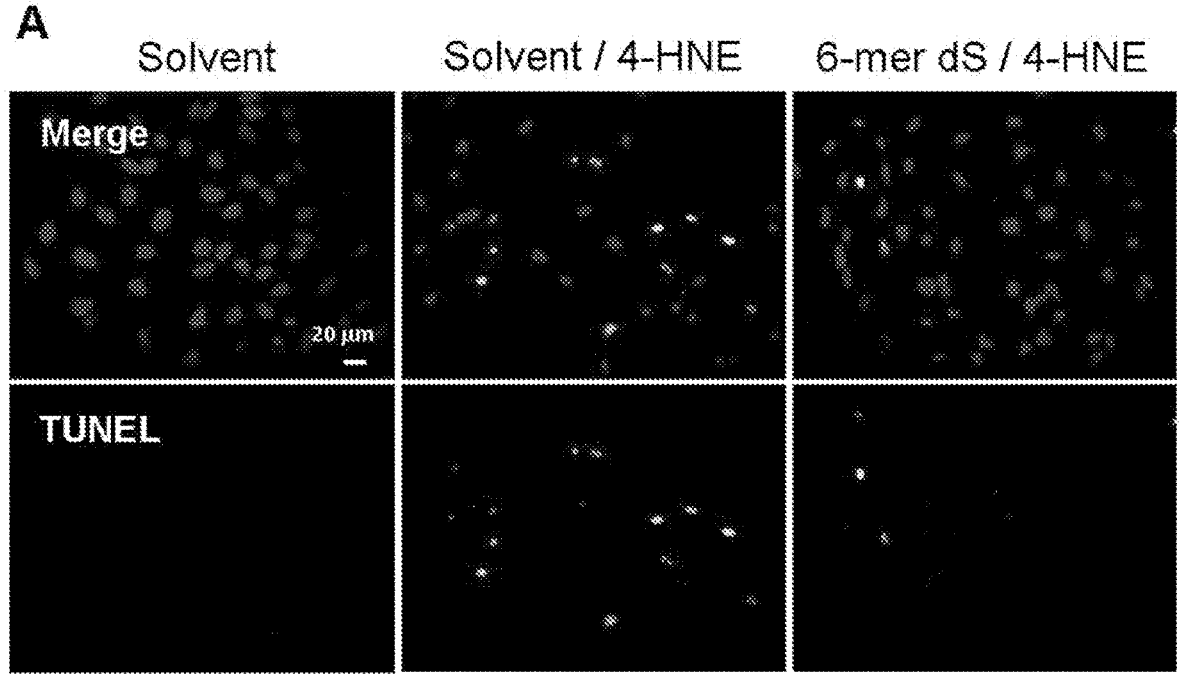
FIG. 6. The protective effect of the 6-mer dS on ARPE-19 cells against 4-HNE induced apoptosis. Cells were deprived of serum for 24 h and then pretreated with 20 μM 6-mer dS or solvent prior to exposed with 25 μM 4-HNE for additional 24 h. Apoptosis was determined by TUNEL staining (green dots) and counter-stained with Hoechst 33258 (blue dots). (A) Representative graphs from three independent experiments are shown. (B) The percentage of cell death was quantified by dividing the number of TUNEL-positive cells to a population of 2000 counted cells per condition. TUNEL, terminal deoxynucleotidyl transferase-mediated dUTP nick end-labeling. $^{a}$P<0.00003 versus solvent-treated cells. $^{b}$P<0.0006 versus solvent/4-HNE-treated cells.
Figure 6:
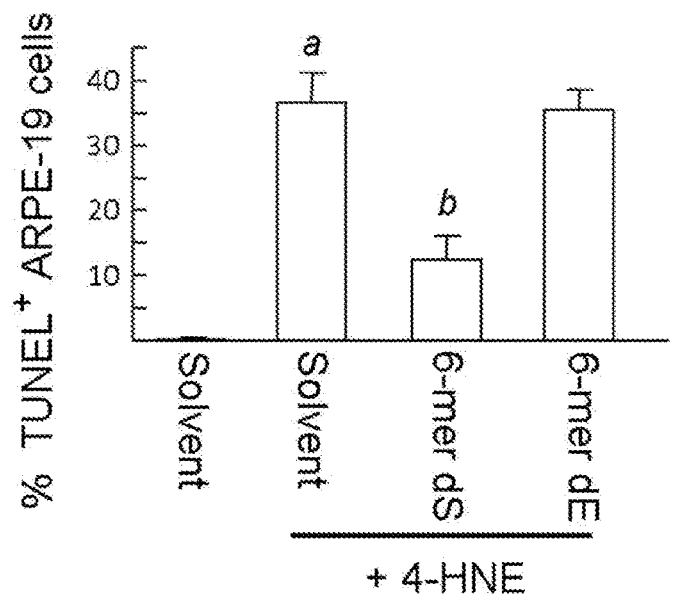

Reference is made to FIG. 6, which depicts the protective effect of 6-mer dS or 6-mer dE on 4-hydroxy-2-nonenal (4-HNE) induced apoptosis of ARPE-19 cells. 4-hydroxy-2-nonenal (4-HNE) is a product of lipid oxidation, and is also considered as one of the most formidable reactive aldehydes capable of forming adduct with various cellular targets, particularly proteins involve in redox signaling. Markedly, 4-HNE has been shown to affect mitochondria by impairing ATPase activity, disrupting oxygen consumption, and eventually triggering premature apoptosis. It was found that 6-mer dS could suppress 4-HNE induced apoptosis, with 6-mer dS being more effective than the 6-mer (FIG. 6, panel B).

Figure 7:
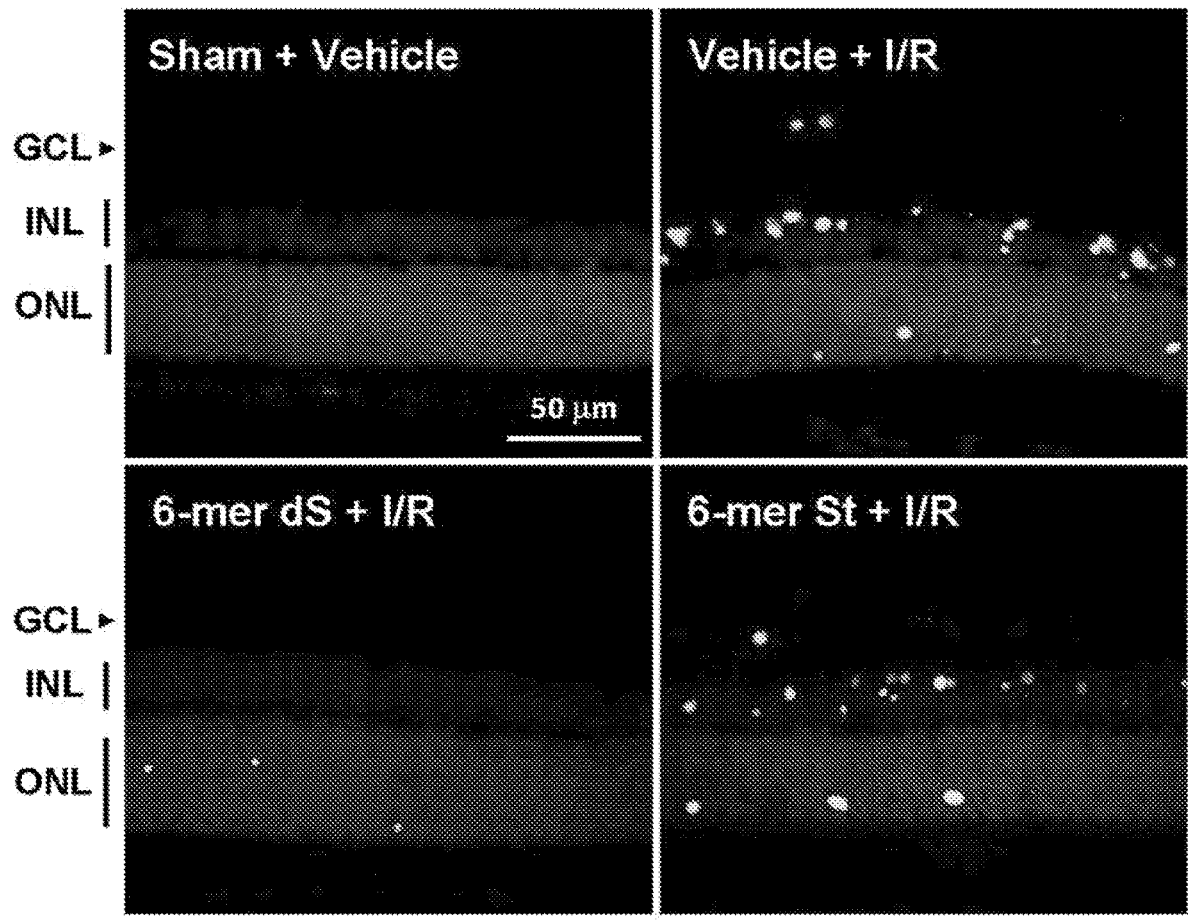
FIG. 7. Representative images of TUNEL stained rat retina from eyes at 20 hours after I/R injury without or with 6-mer variant treatment. The retinal sections were stained with TUNEL (green) and Hoechst 33258 (blue).GCL, ganglion cell layer; INL, inner nuclear layer; ONL, outer nuclear layer.

Images of retina taken from eyes after I/R injury treated with or without 6-mer peptide (6-mer dS or 6-mer St) are provided in FIG. 7. For eyes in the sham group treated with vehicle, the retina cell nuclei were negative for TUNEL staining; and abundant green fluorescent retinal cell nuclei were found within the inner nuclear layer (INL), outer nuclear layer (ONL), and ganglion cell layer (GCL) in the vehicle plus I/R group. By contrast, in the eyes treated with 6-mer dS, only smaller numbers of green fluorescent nuclei were identified by TUNEL staining of the rat retinas, whereas 6-mer St had no such effect (i.e., blocking I/R-induced retinal cell apoptosis). Notably, as summarized in Table 6, the subconjunctival injection of 6-mer Sa, 6-mer Li, 6-mer Gv or 6-mer Qn peptide prior to I/R also reduced the retinal cell apoptosis induced by I/R.

TABLE 6

Quantitative analyses of the number of TUNEL-positive cells in the retina at 20 hours after I/R injury in rat eyes
Number of TUNEL-positive cells in retina (/200 µm)

| | |
|---|---|
| Vehicle + I/R | 27.2 ± 2.7 |
| 6-mer dS + I/R | 7.8 ± 1.5* |
| 6-mer Sa + I/R | 12.6 ± 1.1* |
| 6-mer Li + I/R | 9.8 ± 1.4* |
| 6-mer Gv + I/R | 10.4 ± 1.4* |
| 6-mer Qn + I/R | 12.5 ± 0.89* |
| 6-mer St + I/R | 21.8 ± 1.8 |

Data are expressed as means ± standard deviation (n = 6 eyes per group).
*$P < 0.0001$ versus Vehicle + I/R.

Figure 8:
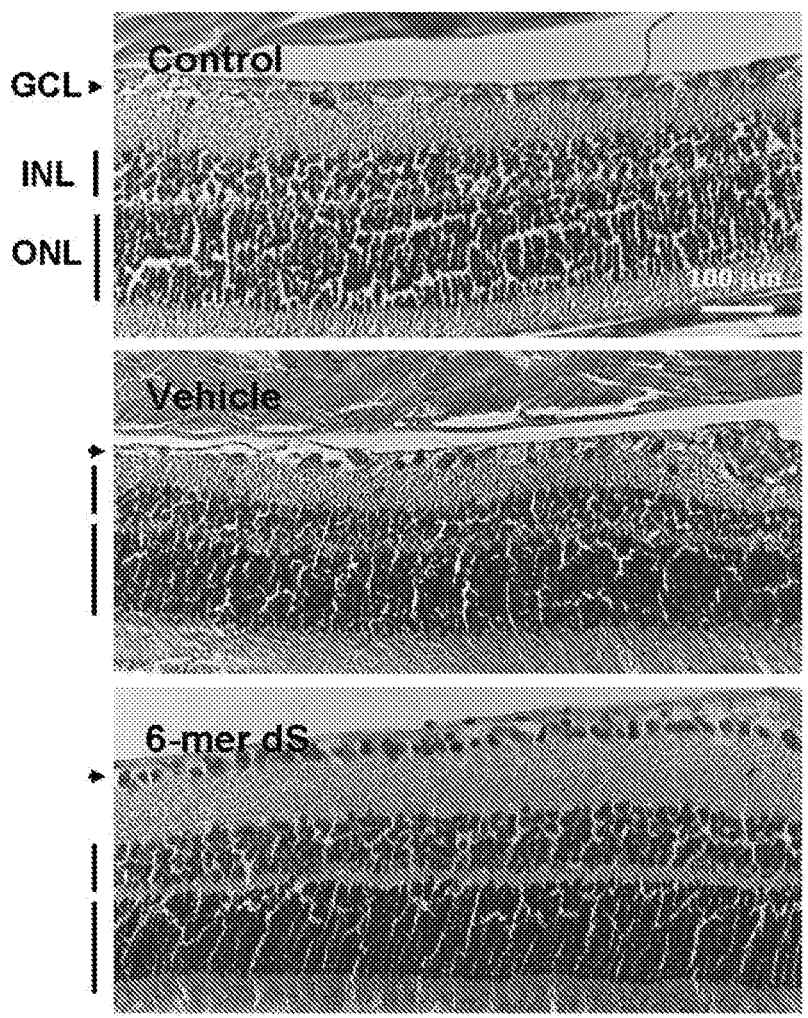
FIG. 8. Representative photographs of hematoxylin and eosin (H&E) stained rat retinal sections from eyes prepared 14 days after I/R injury without or with 6-mer dS treatment.

Reference is now made to FIG. 8, which are photographs of H&E stained retinal sections taken from eyes after I/R injury treated with or without 6-mer dS. After I/R injury for 14 days, H&E stained retinal cross-sections exhibited a reduced retinal thickness (vehicle I/R group) as compared to that in the shame control group. Further, single subconjunctival injection of the 6-mer dS to the I/R injured eyes improved the overall retinal thickness to a level similar to that in the shame control group, suggesting the 6-mer dS treatment can effectively prevent the I/R-induced retinal degeneration. Statistically, the retinal total, INL and ONL thicknesses of 6-mer dS plus I/R group were significantly greater than those in vehicle plus I/R group and comparable to control group (P>0.05) (Table 7). The results further confirm that the 6-mer dS has ability to prevent retinal cell apoptosis induced by I/R at early stage (20 h), thereby keeping the overall retinal thickness following I/R injury for 14 days. These results also suggest that 6-mer variants have a neuroprotective effect to alleviate retinal degeneration.

TABLE 7

Histological examination of retinal atrophy by H&E staining at 14 days after I/R injury

| Total Thickness (From GCL to INL; µm) | | P value |
|---|---|---|
| Control (Uninjured) | 326.2 ± 9.4 | |
| Vehicle + I/R | 260.8 ± 7.1* | *P = 0.006 versus Control |
| 6-mer dS + I/R | 308.9 ± 11.2# | #P = 0.01 versus Vehicle + I/R |
| INL Thickness (µm) | | P value |
| Control (Uninjured) | 70.7 ± 2.4 | |
| Vehicle + I/R | 51.6 ± 0.8* | *P = 0.0003 versus Control |
| 6-mer dS + I/R | 71.3 ± 7.5# | #P = 0.04 versus Vehicle + I/R |
| ONL Thickness (µm) | | P value |
| Control (Uninjured) | 139.8 ± 4.2 | |
| Vehicle + I/R | 125.8 ± 4.5* | *P = 0.04 versus Control |
| 6-mer dS + I/R | 133.4 ± 7.7# | #P = 0.04 versus Vehicle + I/R |

Data are expressed as the means ± standard deviation (n = 6 per group).

Inflammation is a common feature of I/R injury during delayed phase, resulting in further retinal cell death, which in turn, caused blood-retinal barrier (BRB) breakdown. Retinal inflammation is associated with several retinal diseases, such as diabetic retinopathy and glaucoma. The microglia and astrocytes are the resident immune cells of visual system (the retina, optic nerve, and visual centers of the brain) and respond to inflammatory stress as the primary effector cells.

As depicted at FIG. 9, immunofluorescence staining of retinal inflammation at 14 days after I/R injury confirmed a significant activation of Iba-1-positive microglial cells and GFAP-positive astrocytes were found in the I/R injured eyes treated with vehicle, as compared to those in the control group, whereas activation of Iba-1-positive microglial cells and GFAP-positive astrocytes was less prominent in eyes treated with 6-mer dS. In addition, the two inflammatory effectors were found to localize in close proximity to the GCL and along the border of the inner retina of all groups. On average, significantly higher numbers of microglia and astrocytes were noted in vehicle plus I/R group compared to 6-mer dS plus I/R group (Table 8). Collectively, 6-mer dS can effectively suppress the pathologic activation of microglia and astrocytes in retina stimulated by I/R.

TABLE 8

Retinal microglia/astrocytes analysis by Immunofluorescence staining at 14 days after I/R injury

| Iba-1-positive Microglia (/400 × field) | | P value |
|---|---|---|
| Control (Uninjured) | 3.3 ± 1.2 | |
| Vehicle + I/R | 24.7 ± 1.6* | *P = 0.0000002 versus Control |
| 6-mer dS + I/R | 5.8 ± 1.0# | #P = 0.0000004 versus Vehicle + I/R |

TABLE 8-continued

Retinal microglia/astrocytes analysis by Immunofluorescence staining at 14 days after I/R injury

| GFAP-positive Astrocytes (/400 × field) | P value |
|---|---|
| Control (Uninjured) | 6.9 ± 2.0 |
| Vehicle + I/R | 28.6 ± 2.2* *P = 0.000007 versus Control |
| 6-mer dS + I/R | 10.3 ± 1.8# #P = 0.000004 versus Vehicle + I/R |

Data are expressed as the means ± standard deviation (n = 6 per group).

In retinal I/R-injured model, the death of retinal endothelial cells and pericytes leads to acellular capillaries. To determine whether 6-mer dS treatment may effectively protect retinal vasculature after I/R injury, whole-mount retinas were stained with isolectin GS-IB4 (fluorescent-labeled isolectin binding to endothelial cells) and Hoechst 33258 (fluorescent dye for marked cell nucleus). An increase in the number of acellular capillaries was found in the retinas of vehicle-treated I/R injured eyes, as compared to the control retinas obtained from the contralateral eye with sham testing (FIG. 10). The number of degenerate capillaries was reduced by 6-mer dS treatment. Quantitation of the acellular capillaries is summarized in Table 9. Further, sham testing performance in contralateral eye with either vehicle or 6-mer dS had no cytotoxic effect on retinal vasculature. Collectively, 6-mer dS peptide is able to protect against I/R-induced injury to retinal microvasculature.

TABLE 9

The numbers of acellular capillaries in I/R-damaged retinas at 14 days post-ischemia

| Number of acellilar capillaries (/mm²) | P value |
|---|---|
| Sham | N.D. |
| Vehicle + I/R | 7.2 ± 0.9 |
| 6-mer dS + I/R | 2.3 ± 0.7# #P = 0.0001 versus Vehicle + I/R |

Data are expressed as the means ± standard deviation (n = 6 per group).

In sum, results from the I/R animal model studies confirmed that 6-mer variants including 6-mer dS, 6-mer Sa, 6-mer Li, 6-mer Gv, and 6-mer Qn could independently protect the retina against I/R-induced neuronal and vascular damages as well retinal inflammation. Further, animal study suggests that the subconjunctival injection of 6-mer variant may serve as a potential therapeutic option to treat I/R-induced retinal injury.

Example 3 6-mer dS Protects Retinal Vasculature in Diabetic Mice

Microscopic appearance of degenerate capillaries in the I/R-induced retina are similar to that of acellular capillaries found in diabetic retinopathy. To evaluate the possible beneficial effect of 6-mer dS on diabetic retinopathy, the eyes of STZ-induced diabetic mice were topically treated with 6-mer dS or vehicle eye drop three times a day for 14 days. The retinal vascular abnormality was investigated by detecting the extravasation of fluorescein isothiocyanate-bovine serum albumin (FITC-BSA). Microscopic images revealed several hemorrhaging areas in the retina of vehicle-treated diabetic mice (FIG. 11), whereas eyes treated with 6-mer dS eye drop had reduced numbers of vascular lesions (2.8±0.6, 6-mer dS versus 8.2±1.5, vehicle control).

In the retina, endothelial cells, pericytes and astrocytes worked corporately to form the blood-retinal barrier within the intra-retinal capillary network. Astrocytes participate in amplifying the inflammatory response in diabetic mice, which in turn, contributing to vascular leakage in the retina. Reference is made to FIG. 12, in which GFAP immunofluorescence staining of retinas at 14 days after STZ injection showed that a significant activation of GFAP-positive astrocytes were found in the vehicle/STZ group (as compared to control group), whereas they were less prominent in 6-mer dS/STZ group (numbers/400× field: 24.3±2.7 versus 11.0±1.4), indicating that 6-mer dS can effectively suppress the pathologic activation of astrocytes in retina of diabetic mouse.

Non-proliferative diabetic retinopathy (NPDR) unmet treatment needs still exist, which is important in preventing patient from progressing to proliferative diabetic retinopathy (PDR) and/or diabetic macular edema (DME). 6-mer dS eye drop is effective in preventing retinal inflammation and vascular abnormality in early stage of diabetic retinopathy and may enable progression of new therapy to clinical development.

Example 4 6-mer dS Promotes Corneal Wound-Healing

Severe dry eye disease (DED) is usually accompanied with corneal epithelium damaged. In this example, murine dry eye model established according to procedures set forth in "Materials and Methods" section was used to evaluate the therapeutic efficacy of 6-mer variant peptides on the damaged cornea.

Briefly, mice were housed at controlled environment chamber (CEC) for 14 days (set as Day 0) to induce corneal surface disruption. Corneal fluorescein staining was used to estimate the corneal surface injury and the animal with a staining score of 2 (after mice placed at CEC for 14 days) was subjected to peptide treatment. The 6-mer variant peptide formulation for the treatment of DED was described in Methods. After treating with 6-mer dS for 4 days, the results indicated a significant decrease in corneal fluorescein staining compared with its staining score on day 0 (score: 1.4±0.2 versus 3±0; FIG. 13). Treatment with vehicle, 6-mer dA or 6-mer St for 4 days had no therapeutic effect.

It is well known that ocular surface damage is induced and/or promoted by inflammation in the desiccating stress-induced dry eye animals. Among the proinflammatory mediators, suppression of IL-1β and TNF-α have been reported that benefit for amelioration of dry eye in animal. In addition, elevated tear osmolarity is thought to be a core mechanism in the dry eye to induce inflammation and ocular surface damage.

To investigate whether 6-mer variants has ability to suppress the effect of hyperosmotic stress on the proinflammatory gene expression in corneal epithelial cells, rabbit corneal epithelial cells were isolated and expansion in culture, and then treated with 6-mer variant peptide (20 μM) for 6 h prior to cells cultured in a hyperosmotic medium (463 mOsM; by adding 90 mM NaCl). Cells cultured in basal medium (309 mOsm) was used as negative control.

After cells cultured in hyperosmotic medium for 3 h, the mRNA levels of proinflammatory mediators, including TNF-α and IL-1β gene expressions were determined by real-time qPCR. The results showed that TNF-α and IL-1β mRNA were significantly up-regulated by 12.8- and 4.5-fold, respectively, compared to the cells cultured in basal medium (solvent alone) (FIG. 14). However, cells pretreated with 6-mer dS, 6-mer Sa or 6-mer Gv for 6 h apparently repressed the mRNA expression of TNF-α and IL-1β, respectively, compared to the solvent-treated cells.

Inflammation is a major factor in dry eye development. The results confirmed that 6-mer dS, 6-mer Sa and 6-mer Gv may indeed as an anti-inflammatory agent, leading to improved corneal wound-healing.

Taken together, the results presented in the afore-mentioned working examples confirm the short synthetic peptide of the present disclosure possess neuroprotective function, and may be used for the treatment and/or prophylaxis of diseases or conditions related to, neuro degenerative disease (e.g., retinal degenerative disease), and tissue repair and regeneration (e.g., retinal ischemia/reperfusion injury, wound healing, dry eye syndrome, and etc).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A synthetic peptide consisting essentially of the amino acid sequence set forth as $X_1X_2X_3X_4EX_5$ (SEQ ID NO: 1), wherein, $X_1$ is serine(S);

$X_2$ is leucine (L), alanine (A) or isoleucine (I);

$X_3$ is glycine (G), alanine (A), valine (V) or asparagine (N);

$X_4$ is alanine (A), glycine (G) or glutamic acid (E);

$X_5$ is glutamine (Q), alanine (A) or asparagine (N);

$X_2$, $X_3$, $X_4$, and $X_5$ are independently in L-form, while $X_1$ and E are independently in L- or D-form;

in the case when the SEQ ID NO: 1 is the sequence of SLGAEQ (SEQ ID NO: 9), then the serine(S) or the glutamic acid (E) is in D-form; and the N-terminus of the amino acid sequence is acetylated and the C terminus of the amino acid sequence is amidated.

2. The synthetic peptide of claim 1, wherein the synthetic peptide is the amino acid sequence of SEQ ID NO: 9, 13, 14, 15, 17, 19, 20, 21, 22, or 26.

3. A pharmaceutical composition comprising the synthetic peptide of claim 1, and a pharmaceutically acceptable carrier.

4. The pharmaceutical composition of claim 3, wherein the synthetic peptide is the amino acid sequence of SEQ ID NO: 9, 12-13, 14, 15, 17, 19, 20, 21, 22, or 26.

5. The pharmaceutical composition of claim 4, wherein the pharmaceutically acceptable carrier is selected from the group consisting of liquid, gel, cream, and ointment.

6. A method of treating a subject suffering from a retinal degenerative disease or a tissue injury comprising administering to the subject an effective amount of a synthetic peptide consisting essentially of the amino acid sequence set forth as $X_1X_2X_3X_4EX_5$ (SEQ ID NO: 1), wherein, $X_1$ is serine(S);

$X_2$ is leucine (L), alanine (A) or isoleucine (I);

$X_3$ is glycine (G), alanine (A), valine (V) or asparagine (N);

$X_4$ is alanine (A), glycine (G) or glutamic acid (E);

$X_5$ is glutamine (Q), alanine (A) or asparagine (N);

$X_2$, $X_3$, $X_4$, and $X_5$ are independently in L-form, while $X_1$ and E are independently in L- or D-form;

in the case when the SEQ ID NO: 1 is the sequence of SLGAEQ (SEQ ID NO: 9), then the serine(S) or the glutamic acid (E) is in D-form; and the N-terminus of the amino acid sequence is acylated and the C-terminus of the amino acid sequence is amidated wherein the retinal degenerative disease is any of diabetic retinopathy, diabetic macular edema, age-related macular degeneration (AMD), retinitis pigmentosa (RP), glaucoma, or acute UV retinopathy, and wherein the tissue injury is dry eye disease (DED) or retinal ischemia/reperfusion injury.

7. The method of claim 6, wherein the synthetic peptide basis the amino acid sequence of SEQ ID NO: 9, 13, 14, 15, 16, 17, 19, 20, 21, 22, or 26.

8. The method of claim 6, wherein the subject is a human.

* * * * *